United States Patent
Inoue et al.

(10) Patent No.: US 9,326,824 B2
(45) Date of Patent: May 3, 2016

(54) SURGICAL SUPPORT DEVICE

(71) Applicant: OLYMPUS CORPORATION, Tokyo (JP)

(72) Inventors: Shintaro Inoue, Asaka (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 56 days.

(21) Appl. No.: 14/256,056

(22) Filed: Apr. 18, 2014

(65) Prior Publication Data

US 2014/0228862 A1 Aug. 14, 2014

Related U.S. Application Data

(63) Continuation of application No. PCT/JP2012/078552, filed on Oct. 30, 2012.

(30) Foreign Application Priority Data

Nov. 1, 2011 (JP) .................................. 2011-240472

(51) Int. Cl.
*A61B 19/00* (2006.01)
*B25J 9/16* (2006.01)

(52) U.S. Cl.
CPC ........... *A61B 19/2203* (2013.01); *B25J 9/1689* (2013.01); *A61B 2019/2223* (2013.01); *A61B 2019/461* (2013.01); *A61B 2019/465* (2013.01); *A61B 2019/4847* (2013.01); *A61B 2019/4863* (2013.01); *A61B 2019/5259* (2013.01); *G05B 2219/40195* (2013.01); *G05B 2219/45117* (2013.01)

(58) Field of Classification Search
None
See application file for complete search history.

(56) References Cited

U.S. PATENT DOCUMENTS 5,876,325 A * 3/1999 Mizuno et al. ................. 600/102
8,506,555 B2 * 8/2013 Ruiz Morales ................... 606/1
(Continued)

FOREIGN PATENT DOCUMENTS

EP 0 602 657 A2 6/1994
JP 04-256596 A 9/1992
(Continued)

OTHER PUBLICATIONS

International Search Report dated Jan. 8, 2013 issued in PCT/JP2012/078552.
(Continued)

*Primary Examiner* — Jason Holloway
(74) *Attorney, Agent, or Firm* — Scully, Scott, Murphy & Presser, PC

(57) ABSTRACT

A surgical support device includes: a driving member which is moved to transmit a driving force to a target; a first position detection unit and a second position detection unit configured to detect a first and a second moving amounts of the driving member; a difference calculation portion configured to detect a difference in length between the first moving amount and the second moving amount, an operating force computing portion configured to compute a magnitude of a force transmitted to the target from the driving member based on the difference in length; and a breakdown detection portion configured to detect at least one of the first position detection unit and the second position detection unit which has broken down, by use of the first moving amount and the second moving amount.

29 Claims, 13 Drawing Sheets

(56) References Cited

U.S. PATENT DOCUMENTS

| | | | |
|---|---|---|---|
| 2009/0259221 A1* | 10/2009 | Tahara et al. | 606/34 |
| 2010/0057099 A1 | 3/2010 | Fujimoto et al. | |
| 2010/0079099 A1 | 4/2010 | Katsuki et al. | |
| 2010/0234857 A1* | 9/2010 | Itkowitz et al. | 606/130 |
| 2011/0160904 A1* | 6/2011 | Prisco et al. | 700/254 |
| 2013/0090528 A1* | 4/2013 | Ramamurthy et al. | 600/117 |
| 2014/0195052 A1* | 7/2014 | Tsusaka et al. | 700/257 |

FOREIGN PATENT DOCUMENTS

| | | | |
|---|---|---|---|
| JP | 05-253245 A | 10/1993 | |
| JP | 06-168530 A | 6/1994 | |
| JP | 07-223190 A | 8/1995 | |
| JP | 09-179632 A | 7/1997 | |
| JP | 2000-218577 A | 8/2000 | |
| JP | 2001-202134 A | 7/2001 | |
| JP | 2008-259575 A | 10/2008 | |
| WO | 2007/136768 A2 | 11/2007 | |

OTHER PUBLICATIONS

Extended Supplementary European Search Report dated Jun. 29, 2015 from related European Application No. 12 84 5100.2.

* cited by examiner

ND_SURGICAL SUPPORT DEVICE

This application is a continuation application based on PCT Patent Application No. PCT/JP20121078552, filed Oct. 30, 2012, claiming priority based on Japanese Patent Application No. 2011-240472 filed on Nov. 1, 2011 in the Japan Patent Office. The contents of both the PCT Patent Application and the Japanese Patent Application are incorporated herein by reference.

BACKGROUND OF THE INVENTION

1. Field of the Invention

The present invention relates to a surgical support device.

2. Description of Related Art

Typically, as a device for supporting surgery, a surgical support device of a master/slave type including a master unit manipulated by an operator, and a slave unit driven by an operation of the master unit to treat a target to be treated is known.

Such a surgical support device employs a technique capable of operating it during a breakdown. For example, in Japanese Unexamined Patent Application, First Publication No. H05-253245, plural sets of joints of which each angle is changed to each other, and a stand including a driving unit for operating the sets of joints are disclosed. The stand disclosed in Japanese Unexamined Patent Application, First Publication No. H05-253245 is provided with an incremental angle sensor connected to the driving unit, and another angle sensor for detecting an absolute angle of the respective joints.

Even if one angle sensor breaks down in the stand, an angle of the joint can be detected by the other angle sensor. For this reason, it is possible to reliably detect the breakdown of the angle sensor, and to operate such that the stand retreats reliably even when one angle sensor has broken down for example.

In order to reliably operate the surgical support device, it is preferable to prevent a load exceeding an estimation from being applied to the surgical support device, thereby avoiding the breakdown in advance.

The present invention has been made in view of the above matter, and an object of the present invention is to provide a surgical support device that is capable of being reliably operated and has a simple configuration.

SUMMARY OF THE INVENTION

According to a first aspect of the present invention, a surgical support device including a driving member which is moved to transmit a driving force to a target, a first position detection unit configure to detect a first moving amount of the driving member at a predetermined location, a second position detection unit configured to detect a second moving amount of the driving member at a second location different from the predetermined location, a difference calculation portion configured to detect a difference in length between the first moving amount and the second moving amount, an operating force computing portion configured to compute a magnitude of a force transmitted to the target from the driving member based on the difference in length, and a breakdown detection portion configured to detect at least one of the first position detection unit and the second position detection unit which has broken down, by use of the first moving amount and the second moving amount.

According to a second aspect of the present invention, in the surgical support device according to the first aspect, the breakdown detection portion may acquire an instruction value to be sent to a driving force generating unit for moving the driving member, and may compare a first difference value which is a difference value between the instruction value and the first moving amount and a second difference value which is a difference value between the instruction value and the second moving amount, with a threshold value determined based on an amount of expansion/contraction of the driving member in correspondence with the instruction value, thereby the breakdown detection portion may determine that the first position detection unit has broken down when the first difference value is the threshold value or more, and may determine that the second position detection unit has broken down when the second difference value is the threshold value or more.

According to a third aspect of the present invention, in the surgical support device according to the first aspect, the breakdown detection portion may determine that at least one of the first position detection unit and the second position detection unit has broken down when the difference in length is a predetermined range or more.

According to a fourth aspect of the present invention, in the surgical support device according to the third aspect, the breakdown detection portion may acquire an instruction value which is output to a driving force generating unit for moving the driving member in order to instruct a moving amount of the driving member, and when the breakdown detection portion determines that at least one of the first position detection unit and the second position detection unit has broken down, the breakdown detection portion may compare a first difference value which is a difference value between the instruction value and the first moving amount and a second difference value which is a difference value between the instruction value and the second moving amount, with a threshold value determined based on an amount of expansion/contraction of the driving member in correspondence with the instruction value, thereby the breakdown detection portion may determine that the first position detection unit has broken down when the first difference value is the threshold value or more, and may determine that the second position detection unit has broken down when the second difference value is the threshold value or more.

According to a fifth aspect of the present invention, in the surgical support device according to the third aspect, the breakdown detection portion may acquire an instruction value which is output to a driving force generating unit for moving the driving member in order to instruct a moving amount of the driving member, and when the breakdown detection portion determines that at least one of the first position detection unit and the second position detection unit has broken down, the breakdown detection portion may compare a difference value which is a difference value between the instruction value and the second moving amount with a threshold value range having a predetermined upper limit and a predetermined lower limit which are determined based on an amount of expansion/contraction of the driving member in correspondence with the instruction value, thereby the breakdown detection portion may determine that the second position detection unit has broken down when the difference value between the instruction value and the moving amount detected by the second position detection unit is the upper limit or more of the threshold value range, and may determine that the first position detection unit has broken down when the difference value between the instruction value and the second moving amount is within the threshold value range.

According to a sixth aspect of the present invention, in the surgical support device according to any one of the first to fifth aspects, the position detection unit may be configured to stop an operation of the driving member when the breakdown detection portion determines that at least one of the first position detection unit and the second position detection unit has broken down.

According to a seventh aspect of the present invention, in the surgical support device according to any one of the second to sixth aspects, when the breakdown detection portion may determine that at least one of the first position detection unit and the second position detection unit has broken down, when one of the first position detection unit and the second position detection unit which has not broken down, the position detection unit may be configured to move the driving member to a predetermined position while a position of the driving member is detected by the position detection unit which has not broken down; and, after the driving member is moved to the predetermined position, the position detection unit may be configured to stop the driving member.

According to an eighth aspect of the present invention, the surgical support device according to any one of the first to seventh aspects may further include an operating force computing portion configured to determine an excessive load state when the magnitude of the force computed by the computing unit is exceeds an upper limit of a predetermined appropriate load.

According to a ninth aspect of the present invention, the surgical support device according to any one of the first to eighth aspects may further include a surgical instrument configured to perform a treatment on the target, and a slave arm configured to be detachably connected to the surgical instrument, wherein the driving member, the first position detection unit, and the second position detection unit may be provided on the slave arm.

According to a tenth aspect of the present invention, in the surgical support device according to the ninth aspect, the breakdown detection portion may refer to a threshold value determined in advance based on the amount of expansion/contraction of the driving member in correspondence with the first moving amount, and when the difference in length is the threshold value or less, the breakdown detection portion may determine that the surgical instrument has broken down.

According to an eleventh aspect of the present invention, in the surgical support device according to any one of the first to tenth aspects, the surgical support device may be attached to or detached from an articulated arm for supporting the surgical support device.

DETAILED DESCRIPTION OF THE INVENTION

First Embodiment

Figure 1:
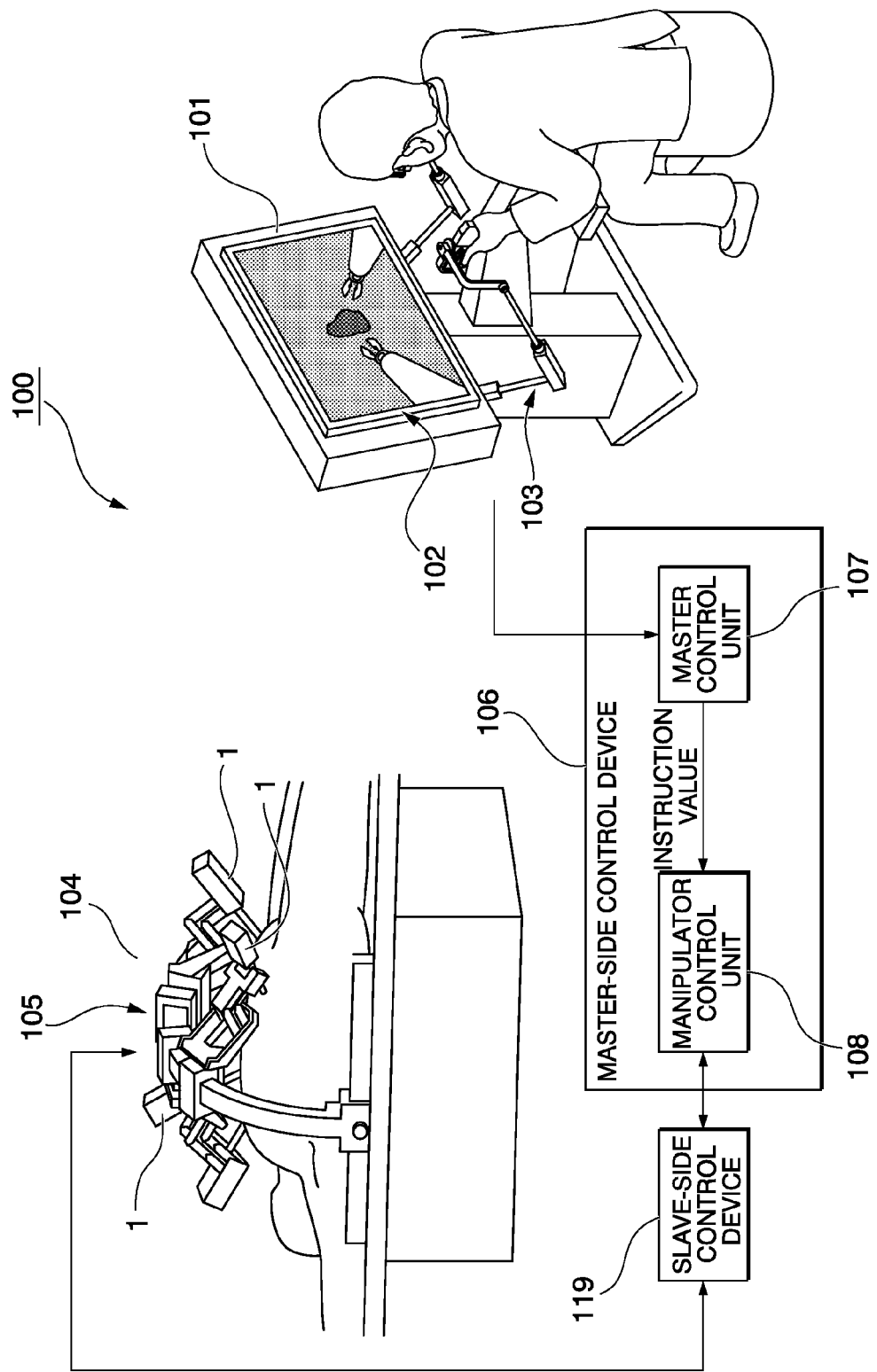
FIG. 1 is an overall view showing the configuration of a surgical support system including a surgical support device of a first embodiment of the present invention.
Figure 2:
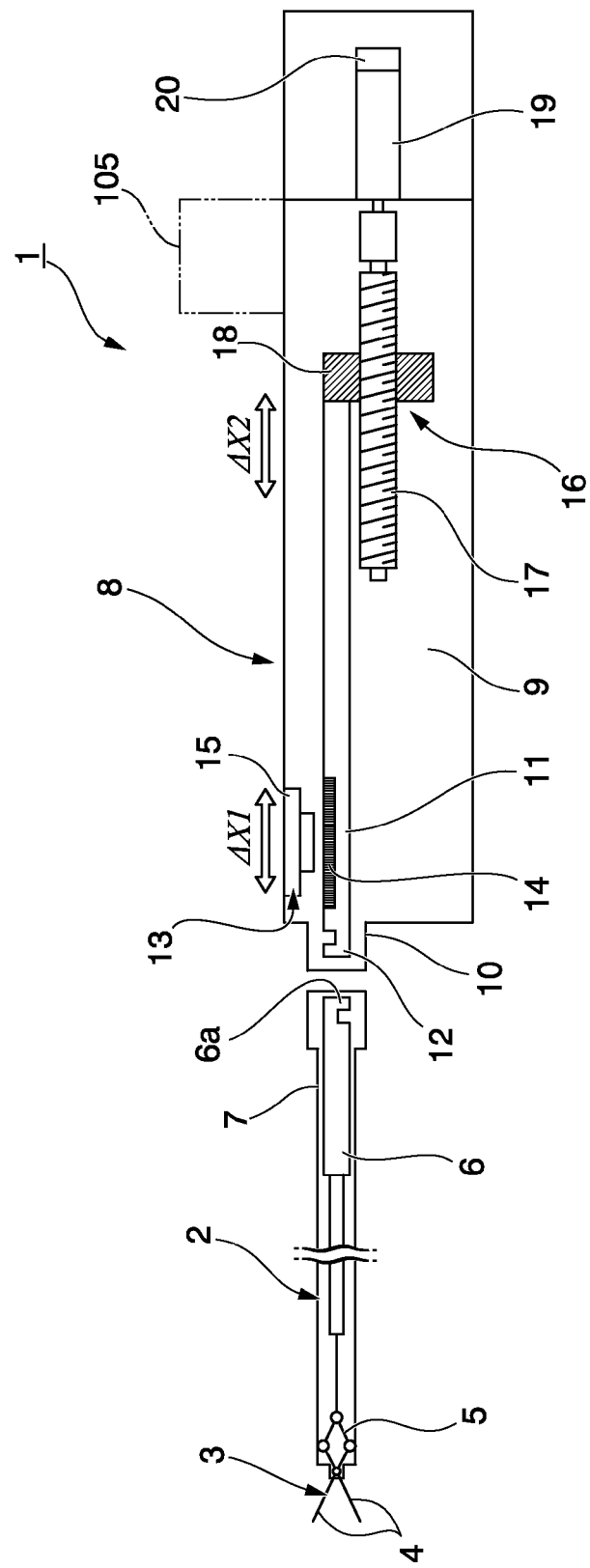
FIG. 2 is a schematic diagram showing the surgical support device.
Figure 3:
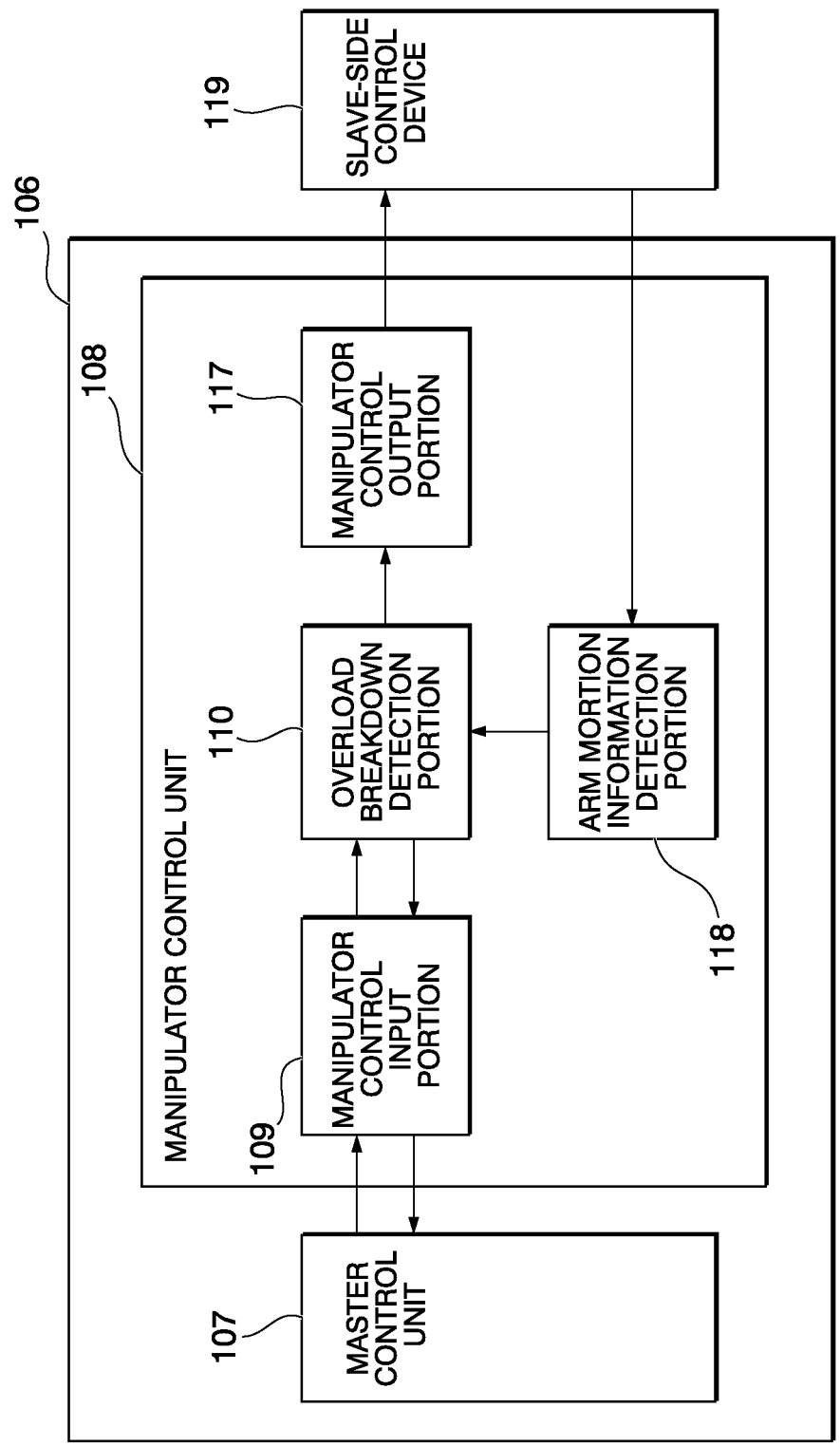
FIG. 3 is a block diagram showing a configuration of a manipulator control unit
Figure 4:
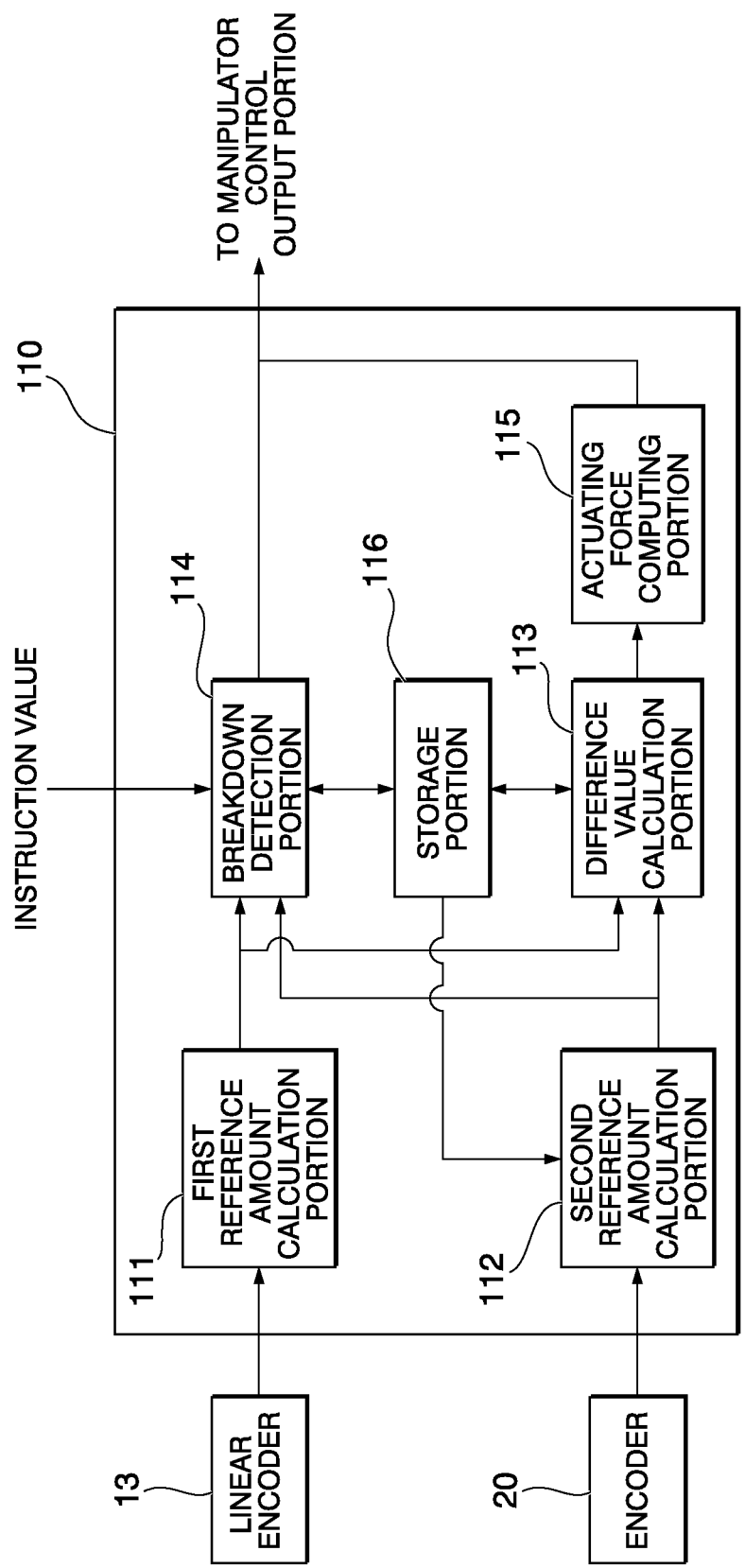
FIG. 4 is a block diagram showing in detail a configuration of an overload breakdown detection unit, which is installed in the manipulator control unit

Hereinafter, a surgical support device according to a first embodiment of the present invention will be described. FIG. 1 is an overall view showing the configuration of a surgical support system including a surgical support device. FIG. 2 is a schematic diagram showing the surgical support device. FIG. 3 is a block diagram showing in detail a configuration of a manipulator control unit. FIG. 4 is a block diagram showing a configuration of an overload breakdown detection unit, which is installed in the manipulator control unit.

As shown in FIG. 1, a surgical support device 1 according to this embodiment can be preferably applied to a surgical support system 100 of a master/slave type. The surgical support system 100 includes a master operation input device 101, a slave manipulator 104, a master-side control device 106, and a slave-side control device 119.

The master operation input device 101 functions as a master configured to transfer a motion of an operator's manipulation to the slave manipulator 104, and includes a master display unit 102 and a manipulation unit 103.

The master display unit 102 is a device configured to display a video of a surgery portion of a patient and the vicinity thereof which is taken by a camera (not shown). The master display unit 102 can be appropriately selected from display devices known in the art, such as a liquid crystal display or an organic EL display, and employed.

The manipulation unit 103 is a mechanism configured to transfer the motion of the operator's manipulation to the slave manipulator 104, and is communicably connected to the master-side control device 106. Also, the manipulation unit 103 is disposed in front of the master display unit 102 so that the operator can manipulate the manipulator while looking at the master display unit 102. When the operation unit 103 is manipulated by the operator, the manipulation unit 103 analyzes the motion of the manipulation, and outputs a manipulation signal to drive the slave manipulator 104 to the master-side control device 106.

The slave manipulator 104 includes a plurality of surgical support devices 1 and an articulated robot 105 for operating the respective surgical support devices 1. Also, only one surgical support device 1 may be provided in the slave manipulator 104.

The respective surgical support devices 1 and the respective articulated robots 105 include a plurality of movable portions which are subjected to be controlled by the slave-side control devices 119. Each movement is controlled based on a control signal output from the slave-side control device 119.

As shown in FIG. 2, the surgical support device 1 includes a surgical instrument 2, a slave arm 8, and an overload breakdown detection portion 110 (see FIG. 3) provided in the master-side control device 106.

In this embodiment, the surgical support device 1 is installed in a shape of an elongated shaft as a whole, of which one end side faces the patient when in use. For this reason, hereinafter, in the case of displaying a relative position of the surgical support device 1 in an axial direction for the respective members of the surgical support device 1, a direction facing the patient when in use is referred to as a distal end side, and a direction opposite to the distal end side is referred to as a proximal end side, unless otherwise mentioned herein.

The surgical instrument 2 may employ a known surgical operation instrument for use in various operations in the inside of a body or in the vicinity of a surgically operated portion for a surgical operation. The surgical instrument 2 is configured to be attached to or detached from a slave arm 8. Also, the surgical instrument 2 may include a movable portion, or may not include the movable portion. In addition, when the surgical instrument 2 is provided with the movable portion, the movable portion may be an operating portion which is operated in direct contact with a patient or another surgical instrument 2, or simply may be a movable instrument in the surgically operated portion.

Concrete examples of the surgical instrument 2 may include treatment tools, such as a needle holder, scissors, an electric scalpel, and an ultrasonic treatment tool, and forceps.

Hereinafter, a case in which the surgical instrument 2 grasps a surgically operated portion or the other surgical instrument 2 will be described as an example.

In this instance, the surgical instrument 2 may be provided integrally with the slave arm 8.

The surgical instrument 2 includes a grasping portion 3, a driving link 5, and a driven portion 6 in that order from the distal end side facing the patient to the proximal end side which is connected to the slave arm 8. The driving link 5 and the driven portion 6 are accommodated in a surgical instrument casing 7 which has a cylindrical shape.

The grasping portion 3 has, for example, grasping arms 4 which are installed to be opened or closed. When the grasping arms 4 are closed, the grasping portion 3 is a mechanism configured to grasp an object to be grasped between the grasping arms 4.

The driving link 5 is a link mechanism configured to open or close the grasping portion 3.

The driven portion 6 is a rod-shaped member for advancing or retracting a primitive segment of the driving link 5 in an axial direction of the housing 7 by a driving force transferred from a driving rod 11, which will be described later, installed in the slave arm 8, when the surgical instrument 2 is connected to the slave arm 8.

One end of the driven portion 6 is connected to the primitive segment of the driving link 5. Also, the other end of the driven portion 6 is provided with a coupling portion 6a for coupling the driving rod 11 and the driven portion 6. The driven portion 6 is made of a high rigidity material, such as metal, so that the driven portion does not buckle even when compression or tension is applied thereto by the driving force transmitted from the driving rod 11, which will be described later, during use, and an amount of expansion or contraction is decreased.

The slave arm 8 constitutes a device body configured to hold the surgical instrument 2, and has an arm housing 9 of a cylindrical shape. A fitting portion 10 which is fitted into a proximal end side of the surgical instrument housing 7 of the surgical instrument 2 is provided with one end of the arm housing 9 in an axial direction. Also, an outer circumference of the arm housing 9 is connected to an end portion of the articulated robot 105. For this reason, as the articulated robot 105 is driven, a position or orientation of the slave arm 8 can be changed depending upon a degree of freedom of the articulated robot 105.

In this embodiment, the driving rod 11 (driving member), a linear encoder 13, a linear motion mechanism 16, a motor 19 (driving force generating unit), and an encoder 20 are provided in the slave arm 8.

The driving rod 11 is formed in the shape of a shaft, and a member which is moved to transmit the driving force to the surgical instrument 2. One end portion, which is an end of a distal end side, of the driving rod 11 in the axial direction is provided with a coupling portion 12 which is connected with the coupling portion 6a of the driven portion 6 in an attachable or detachable manner. Also, the other end portion, which is an end of a proximal end side, of the driving rod 11 in the axial direction is supported by the proximal end side of the slave arm 8 via the motor 19 and the linear motion mechanism 16 which advances and retracts the driving rod 11 in the axial direction.

Moreover, the coupling portion 12 of the driving rod 11 is positioned in the fitting portion 10 when being attached to or detached from the surgical instrument 2.

In this instance, the configuration of the coupling portion 12 is schematically shown in FIG. 2, and is not specifically limited, as long as the driven portion 6 and the driving rod 11 can be attached to or detached from each other and be coupled to each other without wobbling in the axial direction. For example, a configuration of the coupling portion 12 is a configuration in which they are attached to or detached from each other in the axial direction using a concave-convex fitting structure, or a configuration of the coupling portion 12 is a configuration in which they are screw-jointed with each other using a female threaded portion and a male threaded portion may be employed.

In this embodiment, the proximal end portion of the driving rod 11 is connected to a linear motion block 18, of the linear motion mechanism 16 which will be described later. A connecting method thereof includes a method by which the driving block is screwed into the linear block 18, or a method by which the driving block is pressed into the linear motion block 18, and other methods, such as caulking, welding, or screw fixing using connecting inserting. In such a connecting method, the proximal end portion of the driving rod 11 is restricted by the linear motion block 18 or the like over some length. Hereinafter, the word 'proximal end of the driving rod 11' means a position of the most proximal end side which can be subjected to extension or contraction without being restricted by the linear motion block 18 or the like. For example, for the protruding portion of the driving rod 11 from the linear motion block 18, the position of the most proximal end side is referred to as a proximal end of the driving rod 11.

The driving rod 11 is made of a material which can be elastically deformed at least in the axial direction. Moreover, the driving rod 11 is shaped so that the driving rod 11 is not a state of buckling or plastic deformation even when the driving rod 11 is subjected to compression or tension by the counteraction from the driven unit 6 or the driving force received from the linear motion mechanism 16 during use. For example, as a material of the driving rod 11, a metal material such as stainless steel can be preferably employed.

The amount of expansion or contraction of the driving rod 11 in the axial direction may be a degree of which the change in expansion or contraction can be measured with high accuracy by a resolution capability of the linear encoder 13. That is, when the resolution capability of the linear encoder 13 is high, the amount of expansion or contraction of the driving rod 11 in the axial direction may be small, and the loss in transmission of the driving force by the driving rod 11 can be decreased.

In this embodiment, a cross-sectional shape perpendicular to an axis of the driving rod 11 is uniform, except for the coupling portion 12. For this reason, when a force acts on both end portions of the driving rod 11 in a direction facing the axial direction of the driving rod 11, the driving rod 11 is uniformly elastically deformed along the axial direction. In this instance, the cross-sectional shape perpendicular to an axis of the driving rod 11 is not particularly limited thereto. For example, the cross-sectional shape in perpendicular to an axis of the driving rod 11 may be formed in a circular or polygonal shape. Also, the cross-sectional shape in perpendicular to an axis of the driving rod 11 may be a solid section or a hollow section.

With the above configuration, the driving rod 11 can transmit the force in the axial direction between the surgical instrument 2 and the slave arm 8.

The linear encoder 13 is a first position detection unit configured to detect a displacement (first moving amount) of the distal end side point at any one of two points which are spaced apart from each other in the axial direction on the driving rod 11. The linear encoder 13 has a scale portion 14 formed with a pattern for detecting an amount of displacement, and a detection portion 15 configured to detect an amount of relative displacement between the scale portion 14.

The linear encoder 13 may be an incremental type or an absolute value type, but the incremental type linear encoder will be described in this embodiment.

As long as the detecting method of the linear encoder 13 has the resolution capable of detecting the displacement of the driving rod 11 with high accuracy, it is not particularly limited thereto. For example, an optical type or magnetic type linear encoder 13 can be employed. In particular, since the optical type linear encoder using an LED light source obtain high resolution by micronizing a pattern pitch of the scale portion, it is particularly preferable.

An optical type linear encoder 13 is employed in this embodiment. A preferable example of the optical type linear encoder may include, for example, a micro linear encoder ML-08/1000GA (trade name; manufactured by Canon Inc.). In this product, the resolution capable of 0.8 nm can be obtained by setting a lattice pitch of the scale portion is 1.6 μm, and the number of segments is 1000.

The linear encoder 13 is a device configured to measure the displacement of the driving rod 11 to the arm housing 9 of the slave arm 8. Therefore, when any one of the arm housing 9 and the driving rod 11 is provided with the scale portion 14, the other one either of the arm housing 9 or the driving rod 11 is provided with the detection portion 15.

In this embodiment, the scale portion 14 is fixed to a lateral surface of the driving rod 11 which is the vicinity of the proximal end side of the coupling portion 12. When the driven portion 6 is moved within a movable range, the driving rod 11 moves in cooperation with the movement, so that the scale portion 14 is also moved with the driving rod 11.

The length of the scale portion 14 in the axial direction is set to be longer than the maximum movable range of the driven portion 6 connected to the driving rod 11 when use. In this way, no matter where the driven portion 6 is moved to within the movable range of the driven portion 6, it is possible to detect the movement of the driven portion 6.

The detection portion 15 is fixed at a position which is constantly opposite to the scale portion 14 even when the driven portion 6 is moved within the movable range of the driven portion 6. The detection portion 15 detects an amount of movement of the pattern formed on the scale portion 14. Also, the detection portion 15 is configured to be electrically connected to the slave-side control device 119 to output a pulse signal to the slave-side control device 119 in accordance with the displacement of the scale portion 14.

A ball-screw type mechanism is employed as the linear motion mechanism 16. Specifically, the linear motion mechanism 16 includes a ball screw 17 of which a center axis extends in parallel with the axial direction of the arm housing 9, and the linear motion block 18 screw jointed with the ball screw 17.

An end portion of the ball screw 17 at the proximal end side is connected to the motor 19 via a motor rotation shaft and a rotational joint. Accordingly, when the motor 19 is rotated, the ball screw 17 is rotated around the center axis by the rotational force of the motor 19.

The linear motion block 18 is guided by a linear guide member (not shown), which is installed in the slave arm 8, to move along the axial direction of the arm housing 9. The linear motion block 18 is connected to the end portion of the driving rod 11 at the proximal end side. Therefore, when the ball screw 17 is rotated by driving of the motor 19, the linear motion block 18 is advanced and retracted along the ball screw 17. In this way, the driving rod 11 connected to the linear motion block 18 is advanced and retracted in the direction of the center axis of the ball screw 17 by the linear motion block 18.

The motor 19 is a device configured to rotate the ball screw 17 of the linear motion mechanism 16, and is fixed to a fixing member (not shown) installed in the proximal end portion of the arm housing 9. Also, the motor 19 is electrically connected to the slave-side control device 119, and can be rotated at a rotational angle in accordance with the control signal from the slave-side control device 119.

Also, the motor 19 is connected to the encoder 20 above described. The rotational angle of the rotation shaft of the motor 19 can be detected by the encoder 20. In this embodiment, the rotation shaft and the ball screw 17 are directly connected to each other by a rotation joint. Therefore, the rotational angle detected by the encoder 20 coincides with the rotational angle of the ball screw 17.

The encoder 20 is electrically connected to the slave-side control device 119. The encoder 20 outputs information of the detected rotational angle to the slave-side control device 119.

The information of the rotational angle output to the slave-side control device 119 is used for controlling the rotational movement of the motor 19 by the slave-side control device 119. That is, a servo mechanism for the motor 19 is composed of the motor 19 and the slave-side control device 119.

The rotational angle of the rotation shaft detected by the encoder 20 can be converted into a moving amount of the linear motion block 18 using, for example, the transfer pitch of the ball screw 17. That is, the encoder 20 constitutes a drive amount detector configured to detect a drive amount of the advance and retract drive. The moving amount of the linear motion block 18 represents the displacement of the point on the proximal end portion of the driving rod 11 which is connected to the linear motion block 18.

Accordingly, the encoder 20 constitutes a second position detection unit configured to detect the displacement (second moving amount) of any one, at the proximal end side, of two points which are spaced apart from each other in the axial direction on the driving rod 11.

With the above configuration, the linear motion block 18 and the motor 19 constitute a driving unit configured to advance and retract the proximal end portion of the driving rod 11 in the axial direction.

As shown in FIG. 3, the master-side control device 106 includes a master control unit 107 and a manipulator control unit 108. The master control unit 107 receives a manipulation signal output from the master operation input device 101 (see FIG. 1), and interprets the drive amount of the movable portion which is a target controlled by the slave manipulator 104 to achieve the movement based on the manipulation signal. In addition, the master control unit 107 outputs a movable portion selection signal to select the movable portion which is a target to be controlled, and an instruction value for the movable portion, which is selected by the movable portion selection signal, to the manipulator control unit 108, based on the manipulation signal.

The manipulator control unit 108 includes a manipulator control input portion 109, an overload breakdown detection portion 110, a manipulator control output portion 117, and an arm motion information detection portion 118.

The movable portion selection signal and the instruction value is input to the manipulator control input portion 109 from the master control unit 107. Also, the manipulator control input portion 109 outputs a notification signal, which will be described later, transmitted from the overload breakdown detection portion 110 to the master operation input device 101.

As shown in FIG. 4, the overload breakdown detection portion 110 includes a first reference amount calculation portion 111, a second reference amount calculation portion 112, a difference value calculation portion 113, a breakdown detection portion 114, an operating force computing portion 115, and a storage portion 116.

The first reference amount calculation portion 111 is electrically connected to the linear encoder 13, and detects displacement $\Delta X1$ (see FIG. 2) of a point, at the distal end side, of two points which are spaced apart from each other in the axial direction on the driving rod 11 from the output of the linear encoder 13. The displacement $\Delta X1$ detected by the first reference amount calculation portion 111 is output to the breakdown detection portion 114 and the difference value calculation portion 113 from the first reference amount calculation portion 111.

In this embodiment, with regard to the positive and negative of the displacement $\Delta X1$, the direction facing from the proximal end side toward the proximal end side is referred to as positive.

The position of an original point when the displacement $\Delta X1$ is detected is determined when the surgical support system 100 starts or in the state in which no load is applied to the surgical instrument 2. At the time of setting the original point, the displacement $\Delta X1$ of the point on the scale portion 14 which is disposed on the unique detection position in the detection portion 15 is detected by the linear encoder 13 reading a passing pattern in the detection position which occurs in accordance with the movement of the point. The detection position is, for example, an illumination position of detection light to the scale portion 14 when the detection portion 15 is the optical type. Since the scale portion 14 is made to have a length sufficiently shorter than the overall length of the driving rod 11, and is made of a material which is not easily deformed, the expansion or contraction of the scale portion 14 can be disregarded. Accordingly, the linear encoder 13 can regard the displacement $\Delta X1$ detected by the scale portion 14 as being constant at every position on the scale portion 14.

The second reference amount calculation portion 112 is electrically connected to the encoder 20, and detects a displacement $\Delta X2$ (see FIG. 2) of a point, at the proximal end side, of two points which are spaced apart from each other in the axial direction on the driving rod 11 from the output of the encoder 20 and output it to the breakdown detection portion 114 and the difference value calculation portion 113.

Information on the rotational angle of the ball screw 17 output from the encoder 20 is input to the second reference amount calculation portion 112. There is a different mechanical error between the rotational angle of the ball screw 17 and the moving amount of the linear motion block 18 for every device. Accordingly, in this embodiment, a correspondence relationship between the rotational angle of the ball screw 17 and the moving position of the point on the proximal end side is actually measured in advance in order to compensate for the unique moving error in the device, and then is stored in the storage portion 116.

The second reference amount calculation portion 112 calculates the displacement using the value output from the encoder 20 and the correspondence relationship stored in the storage portion 116.

Therefore, the second reference amount calculation portion 112 can calculate the displacement of the linear motion block 18. Since the displacement of the linear motion block 18 is equal to the displacement $\Delta X2$ of the point on the proximal end of the driving rod 11 connected to the linear motion block 18, the second reference amount calculation portion 112 can detect the displacement $\Delta X2$ of the point on the proximal end.

The second reference amount calculation portion 112 may be configured to convert the rotational angle of the ball screw 17 into a screw forwarding amount based on a size of a lead of the ball screw.

The difference value calculation portion 113 converts the displacement $\Delta X1$ output from the first reference amount calculation portion 111 and the displacement $\Delta X2$ output from the second reference amount calculation portion 112 into a displacement based on the point when no load is applied to the surgical instrument 2 connected to the slave arm 8. In addition, the difference value calculation portion 113 calculates these difference values to store them in the storage portion 116 and output them to the operating force computing portion 115.

The breakdown detection portion 114 respectively compares the instruction value output from the master control unit 107 in order to operate the slave arm 8 with the displacements $\Delta X1$ and $\Delta X2$ which are calculated by the first reference amount calculation portion 111 and the second reference amount calculation portion 112. Also, a threshold value to represent an allowable limit for the difference between the displacement $\Delta X1$ calculated by the first reference amount calculation portion 111 and the instruction value, and a threshold value to represent an allowable limit for the difference between the displacement $\Delta X2$ calculated by the second reference amount calculation portion 112 and the instruction value are stored in the storage portion 116. The breakdown detection portion 114 is configured to determine whether or not the encoder 20 and the linear encoder 13 have broken down using these threshold values.

That is, when a difference value (first difference value) obtained by subtracting the instruction value from the displacement $\Delta X1$ calculated by the first reference amount calculation portion 111 exceeds the threshold value, the breakdown detection portion 114 determined that the linear encoder 13 has broken down. Furthermore, when a difference value (second difference value) obtained by subtracting the instruction value from the displacement ΔX2 calculated by the second reference amount calculation portion 112 exceeds the threshold value, the breakdown detection portion 114 is determined that the encoder 20 has broken down.

The breakdown detection portion 114 outputs the information that the linear encoder 13 has broken down and the information that the encoder 20 has broken down to the manipulator control output portion 117, respectively. In this instance, the breakdown detection portion 114 can feed the fact that the linear encoder 13 has broken down and the fact that the encoder 20 has broken down back to the manipulator control input portion 109 as the notification signal, respectively.

The operating force computing portion 115 detects a magnitude of the force applied to the driving rod 11 from the slave arm 8 via the surgical instrument 2 or the linear motion block 18 based on the difference value output from the difference value calculation portion 113. When the operating force computing portion 115 determined that the force of the upper limit value or more of an appropriate load is applied to the surgical supporting device 1, the operating force computing portion 115 determines that an excessive load is applied thereto. When the operating force computing portion 115 determines that the excessive load is applied to the surgical supporting device 1, the manipulator control output portion 117 is controlled to restrict the output from the manipulator control output portion 117. Also, the operating force computing portion 115 outputs a signal to display the information indicative of the state, in which the excessive load is applied, to the master display unit 102, and displays an image for enabling an operator to perceive the state in which the excessive load is applied, on the master display unit 102.

The storage portion 116 is electrically connected to the second reference amount calculation portion 112, the difference value calculation portion 113, and the operating force computing portion. A data required for computation processing which is executed by the overload breakdown detection portion 110 is stored in the storage portion 116. The data stored in the storage portion 116 includes, for example, the data to represent the correspondence relationship between the rotational angle of the encoder 20 and the moving position of the point by the ball screw 17, and the upper limit value for the magnitude of the appropriate load in the surgical support device 1, as described above.

The device configuration of the overload breakdown detection portion 110 may include only hardware having the above function. Also, the overload breakdown detection portion 110 may include a computer having a CPU, a memory, an input/output interface, an external memory device, or the like and a program executed by the computer.

The manipulator control output portion 117 is electrically connected to the slave-side control device 119, and outputs a signal to operate the slave manipulator 104 to the slave-side control device 119.

The arm motion information detection portion 118 acquires information on the position of the slave arm 8 installed on the slave manipulator 104, and the articulated robot 105. In this embodiment, the arm motion information detection portion 118 detects the output from the linear encoder 13 and the encoder 20, and outputs them to the overload breakdown detection portion 110.

The slave-side control device 119 is electrically connected to the master-side control device 106 and the slave manipulator 104. The slave-side control device 119 generates, for example, a signal to drive the motor 19 disposed on the slave arm 8 to output it to the motor 19, based on the signal output from the manipulator control output portion 117. In this way, the slave-side control device 119 can operate the surgical instrument 2 using the motor 19.

Figure 5:
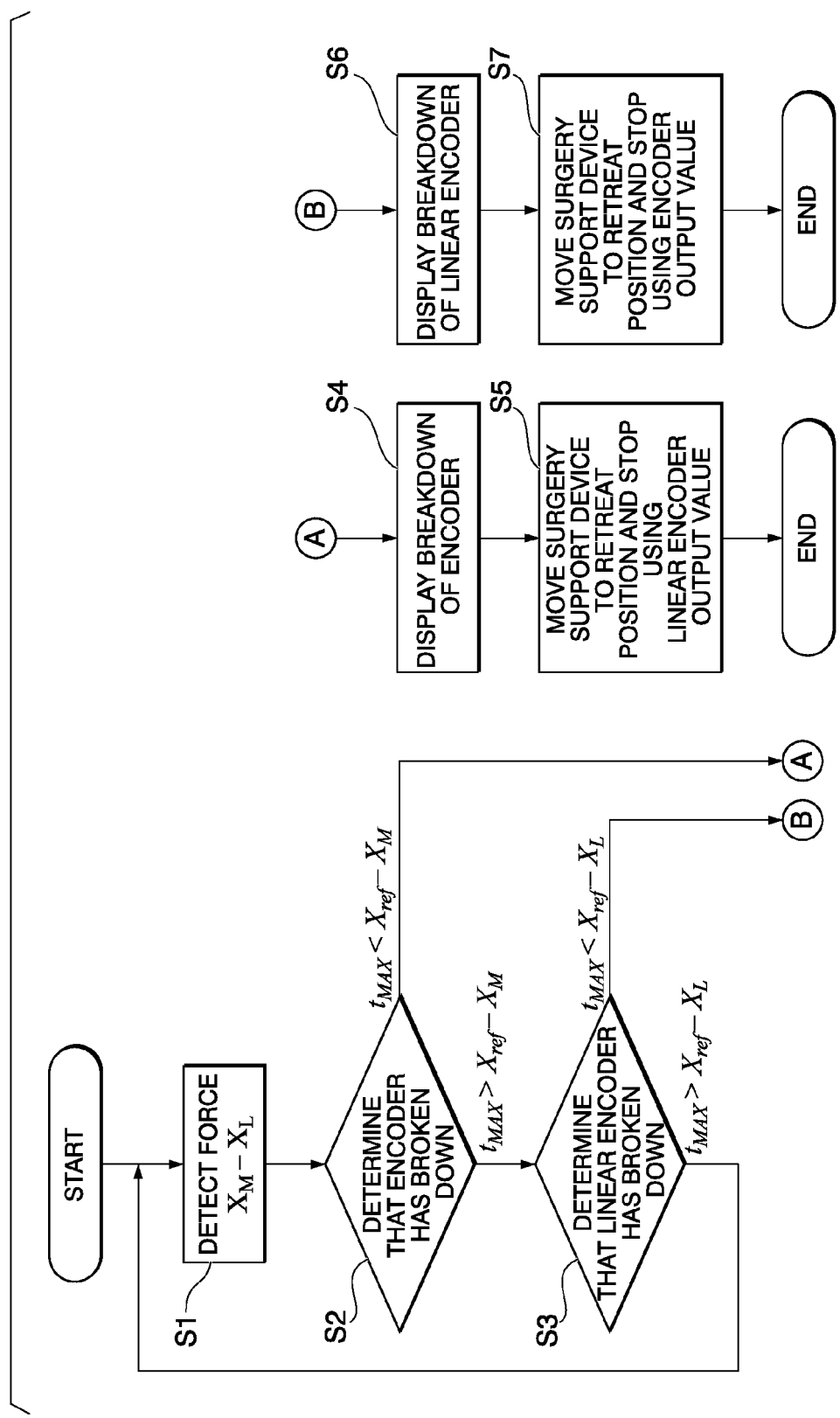
FIG. 5 is a flowchart showing a part of an operation of the surgical support device during an operation of a surgical support system.

Next, the behavior of the surgical support device 1 will be described together with the operation of the surgical support system 100 in use. FIG. 5 is a flowchart showing a part of the operation of the surgical support device during the operation of the surgical support system.

The surgical support device 1 is set to the slave manipulator 104 in the state in which the surgical instrument 2 is attached to the slave arm 8. When the surgical support system 100 starts to operate in the state in which the surgical instrument 2 is connected to the slave arm 8, the surgical support device 1 is initialized. At that time, the original points of the linear encoder 13 and the encoder 20 are respectively reset, and then this position becomes a position of a displacement 0 (ΔX1=0 and ΔX2=0).

When the surgical y instrument 2 is in the unloaded condition at the initialization, the position of the original point determined by the reset becomes a reference of the displacement in the unloaded condition. When it is reset in the state in which the load is applied to the surgical instrument 2 at the initialization, the position of the original point determined by the reset becomes a reference of the displacement when the same load as the load applied at the initialization is applied. In this embodiment, it is preferable that the surgical instrument 2 be in the unloaded condition at the initialization.

Also, the articulated robot 105 is moved to the position previously set at the initialization.

Next, the operator operates the manipulation unit 103 while viewing the video displayed on the master display unit 102 of the master operation input device 101. The manipulation unit 103 interprets the motion of the manipulation by the operator, and transmits the manipulation signal to drive the slave manipulator 104 to the master-side control device 106.

The master-side control device 106 transmits the movable portion selection signal and the instruction value for controlling the operation of the respective movable portions of the slave manipulation 104 from the master control unit 107 to the manipulator control unit 108, based on the manipulation signal. The control signal is transmitted from the manipulator control unit 108 to the slave-side control device 119, based on the movable portion selection signal and the instruction value.

For example, the control signals to perform the operation in which the grasping portion 3 installed on the surgical instrument 2 of the surgical support device 1 is opened, the grasping portion 3 is moved to the position at which the object to be grasped is grasped by the articulated robot 105, and the grasping portion 3 is closed to grasped the object to be grasped are transmitted from the manipulator control unit 108 to the slave-side control device 119.

In this way, the motor 19 of the surgical support device 1 is driven, and then the linear motion block 18 is moved toward the distal end side. The driven portion 6 is moved toward the distal end side via the driving rod 11, and then the grasping portion 3 is opened by the driving link 5.

When the object to be grasped is grasped, the motor 19 is reversely rotated to move the linear motion block 18 to the proximal end side.

The operation of the surgical instrument 2 when the motor 19 is operated is detected by the output from the linear encoder 13 or the encoder 20.

In parallel with the driving operation, the overload breakdown detection portion 110 sequentially computes the force acting on the driving rod 11 based on the amount of displacement of the point on the driving rod 11 which is acquired by the linear encoder 13 and the encoder 20, thereby determining whether the linear encoder 13 or the encoder 20 has broken down or not.

First, the force detection (step S1 shown in FIG. 5) by the overload breakdown detection portion 110 will be described.

When the motor 19 is driven, an output $X_L$ from the linear encoder 13 and an output $X_M$ from the encoder 20 are sequentially input to the first reference amount calculation portion 111 and the second reference amount calculation portion 112. The first reference amount calculation portion 111 and the second reference amount calculation portion 112 output the respective displacements ΔX1 and ΔX2 to the difference value calculation portion 113 based on these output signals. The difference value ($X_M$-$X_L$) calculated by the difference value calculation portion 113 is output to the operating force computing portion 115.

The operating force computing portion 115 computes the magnitude of the force applied to the driving rod 11, based on the difference value calculated by the difference value calculation portion 113. In addition, the operating force computing portion 115 compares the magnitude of the force applied to the driving rod 11 with the upper limit value (threshold value $t_{MAX}$ shown in FIG. 5) of the appropriate load stored in the storage portion 116. When the magnitude of the force is the upper limit value or more of the appropriate load, the operating force computing portion 115 determines that the surgical support device 1 is operating in the overload state. The operating force computing portion 115 which is determined as the overload state outputs to the master display unit 102 the signal to display a warning indicates the state in which the excessive load is applied on the master display unit 102. Furthermore, the control to restrict the driving force for operating the surgical support device 1 may perform on the manipulator control output portion 117. In this way, the surgical support device 1 operates within the range less than the upper limit of the appropriate load.

However, since the surgical support system 100 according to this embodiment is provided with the linear encoder 13 and the encoder 20, the unit for detecting the operating amount of the surgical instrument 2 is duplicated. In this way, whether the linear encoder 13 or the encoder 20 has broken down, it is possible to operate the surgical instrument 2. In this embodiment, when either of the linear encoder 13 and the encoder 20 has broken down, the one of the linear encoder 13 or the encoder 20 that has broken down is specified, and the operation can be continued using the other in a normal state.

When either of the linear encoder 13 or the encoder 20 has broken down, the output from the linear encoder 13 or the encoder 20 is stopped.

The breakdown detection portion 114 performs the breakdown determination of the encoder 20 (step S2 shown in FIG. 5) and the breakdown determination of the linear encoder (step S3 shown in FIG. 5).

In step S2, when the encoder 20 has broken down, since the difference value obtained by subtracting the output $X_M$ of the encoder 20 from an instruction value $X_{ref}$ exceeds above the threshold value $t_{MAX}$ for the breakdown determination, the process proceeds to step S4.

In step S3, in the case where the linear encoder 13 has broken down, since the difference value obtained by subtracting the output $X_L$ of the linear encoder 13 from an instruction value $X_{ref}$ exceeds the threshold value $t_{MAX}$, the process proceeds to step S6.

In this way, the respective breakdown determination of the encoder 20 and the linear encoder 13 can be performed in steps S2 and S3 described above.

In addition, when the breakdown detection portion 114 determines that the encoder 20 has broken down, the breakdown detection portion 114 displays information indicating the fact that the encoder 20 has broken down, on the master display unit 102 (step S4 shown in FIG. 5). In addition, the breakdown detection portion 114 disregards the output of the encoder 20, and allows the surgical support device 1 to continuously operate using the output value of the linear encoder 13. That is, the breakdown detection portion 114 performs the position detection using the output from the linear encoder 13 which operates as usual, and reliably retreats the surgical support device 1 and then, stops the surgical support device 1 (step S5 shown in FIG. 5).

In contrast, when it is determined that the linear encoder 13 has broken down by the breakdown detection portion 114, the breakdown detection portion 114 displays the fact that the linear encoder 13 has broken down on the master display unit (step S6 shown in FIG. 5). In addition, the breakdown detection portion 114 disregards the output from the linear encoder 13, and performs the position detection using the output from the encoder 20 which operate as usual. That is, the breakdown detection portion 114 performs the position detection using the output from the encoder 20 which operate as usual, and reliably retreats the surgical support device 1 and then, stops the surgical support device 1 (step S7 shown in FIG. 5).

In this way, the surgical support device 1 according to this embodiment can specify which of the linear encoder 13 and the encoder 20 has broken down. After one of the linear encoder 13 and the encoder 20 has broken down, the surgical instrument 2 can be operated using the information from the other which operates as usual.

When a different surgical support device 1 to which the same surgical instrument 2 as the broken surgical support device 1 is attached is on the slave manipulator 104, the breakdown detection portion 114 may display information indicating the fact that a replaceable surgical support device 1 is installed, on the master display unit 102.

Furthermore, if it is determined that both the linear encoder 13 and the encoder 20 have broken down by the breakdown detection portion 114, the breakdown detection portion 114 may stop all the operation of the slave manipulator 104 including the operation of the motor 19. After that, the slave manipulator 104 may be reliably retreated by manual work of the operator.

When it is determined that any one of the linear encoder 13 and the encoder 20 has broken down by the breakdown detection portion 114, the breakdown detection portion 114 may stop all the operation of the slave manipulator 104. In this instance, since the operation of the driving rod 11 is also stopped, the position and orientation of the surgical instrument 2 are fixed.

As described above, the surgical support device 1 according to this embodiment can perform the force detection using the linear encoder 13 and the encoder 20 which detect the displacement. When the stretch of the driving rod 11 in correspondence with the instruction value output to the motor 19 is not detected, it may be determined that the linear encoder 13 or the encoder 20 has broken down by using the correspondence relationship between the magnitude of the force applied to the driving rod 11 from the motor 19 and the stretch of the driving rod 11. For this reason, it is possible to reliably operate the surgical support device 1 and also simplify the configuration.

In addition, since the breakdown detection portion 114 can specify the broken one of the linear encoder 13 and the encoder 20, the surgical support device 1 can continuously perform the position detection using the other one which has not broken down. Therefore, when any one of the linear encoder 13 and the encoder 20 operates as usual, the surgical support device 1 can be reliably retreated by operating the motor 19.

Second Embodiment

Figure 6:
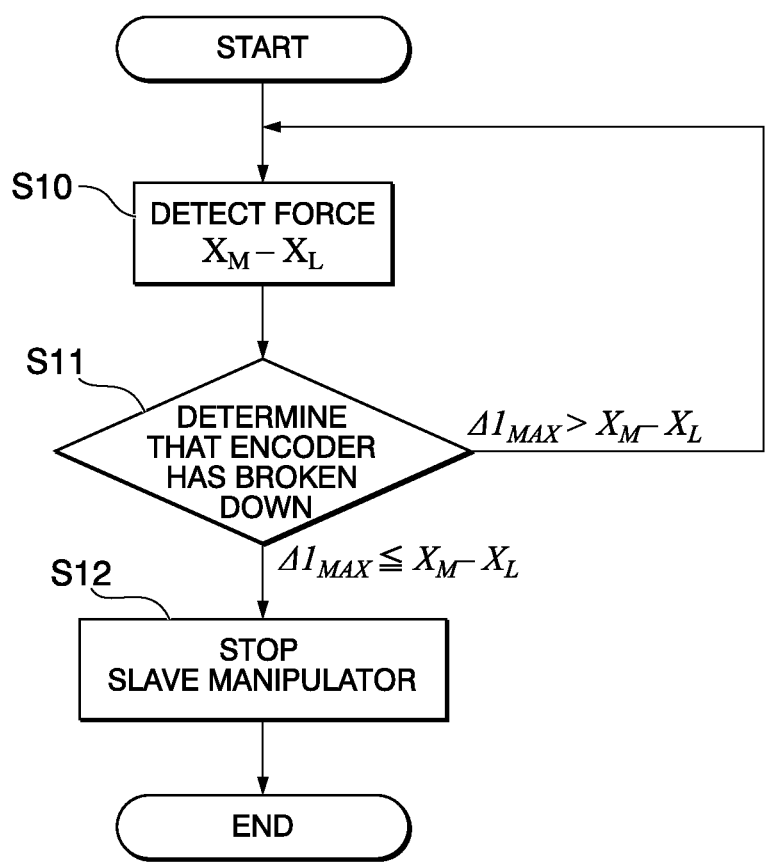
FIG. 6 is a flowchart showing an operation of a surgical support device of a second embodiment of the present invention.

Next, a surgical support device 1 according to the second embodiment of the present invention will be described. In this instance, in the respective embodiments described hereinafter, the same configuration as those of the surgical support device 1 according to the first embodiment described above are denoted by the same reference numerals, and description thereof will be omitted. FIG. 6 is a flowchart showing an operation of the surgical support device according to this embodiment.

In this embodiment, a breakdown detection method by the breakdown detection portion 114 is different from the first embodiment.

In this embodiment, an amount of expansion or contraction of the driving rod 11 is detected by comparing the value output from the linear encoder 13 with the value output from the encoder 20. That is, in this embodiment, the instruction value to drive the motor 19 is not used for the breakdown determination of the linear encoder 13 and the encoder 20.

The breakdown detection portion 114 compares the displacement ΔX1 calculated by the first reference amount calculation portion 111 with the displacement ΔX2 calculated by the second reference amount calculation portion 112, and calculates the difference value. A threshold value $\Delta I_{MAX}$ for the difference value is stored in the storage portion 116. When the difference value calculated by the breakdown detection portion 114 is the threshold value $\Delta I_{MAX}$ or more stored in the storage portion 116, the breakdown detection portion 114 determines that either of the linear encoder 13 and the encoder 20 has broken down (step S11 shown in FIG. 6).

In this embodiment, when it is determined that either of the linear encoder 13 and the encoder 20 has broken down by the breakdown detection portion 114, the broken one of the linear encoder 13 and the encoder 20 is not specified, and all operation of the slave manipulator 104 is stopped (step S12 shown in FIG. 6).

The breakdown detection method also produces the same effect as that of the first embodiment.

In addition, in this embodiment, since the breakdown determination can be performed using only the amount of expansion or contraction of the driving rod 11, it is possible to further simplify the configuration.

In general, in the manipulator performing the position control, when the load is generated on the driving shaft or an abrupt change occurs in the instruction position, there is a case in which a deviation between the instruction position and the detected position is temporarily increased. In this embodiment, the breakdown determination is performed by the difference between the displacement ΔX1 calculated by the first reference amount calculation portion 111 and the displacement ΔX2 calculated by the second reference amount calculation portion 112. As the result, it is possible to suppress a false detection of the breakdown due to the increase in the deviation.

First Modified Example

Although the second embodiment describes the example in which the broken one of the linear encoder 13 and the encoder 20 is not specified, the broken device may also be specified.

This modified example utilizes the threshold value $t_{MAX}$ which is determined in advance based on the amount of expansion or contraction of the driving rod 11 in correspondence with the instruction value $X_{ref}$ output to the slave arm 8 from the master control unit 107, in order to specify which of the linear encoder 13 and the encoder 20 has broken down.

Figure 7:
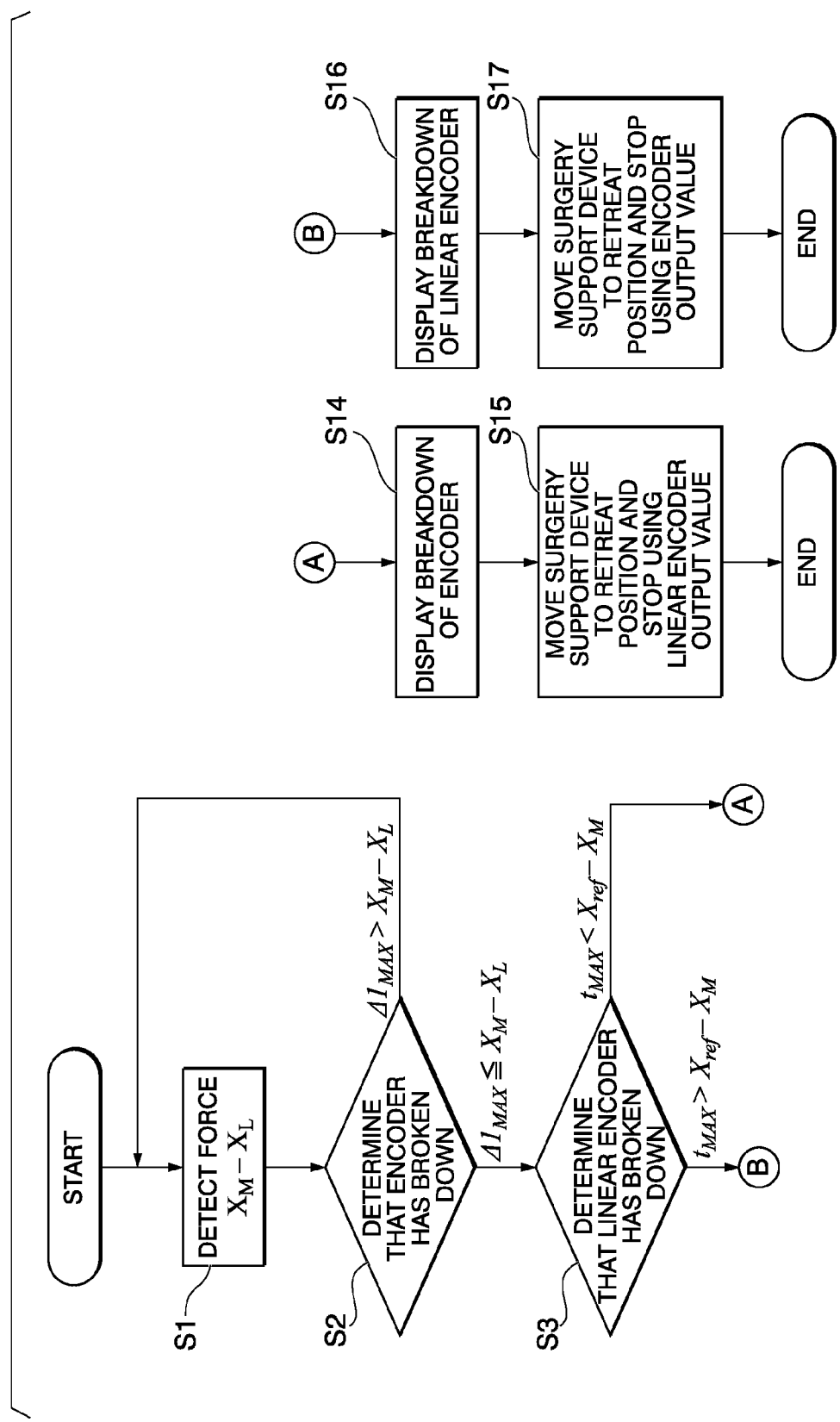
FIG. 7 is a flowchart illustrating the operation of the surgical support device of a first modified example of the second embodiment of the present invention.

When the case where the difference value obtained by subtracting the output $X_M$ of the encoder 20 from the instruction value $X_{ref}$ is the threshold value $t_{MAX}$ or more, the breakdown detection portion 114 determines that the encoder 20 has broken down, and then the process proceeds to step S14 (step S13 shown in FIG. 7).

When the difference value obtained by subtracting the output $X_M$ of the encoder 20 from the instruction value $X_{ref}$ is below the threshold value $t_{MAX}$, the breakdown detection portion 114 determines that the encoder 20 has not broken down (step S13 shown in FIG. 7). If the process proceeds from step S11 to step S13, any one of the linear encoder 13 and the encoder 20 has broken down. Therefore, in this case, the linear encoder 13 has broken down. When the breakdown detection portion 114 determines that the encoder 20 has not broken down in step S13, the process proceeds to step S16.

When it is determined that the linear encoder 13 or the encoder 20 has broken down by the breakdown detection portion 114, the breakdown of the respective encoders 13 and 20 is displayed on the master display unit 102, like the first embodiment (steps S14 and 16 shown in FIG. 7). After that, the surgical support device 1 is reliably retreated using the output value from the other of the linear encoder 13 and the encoder 20 which operates as usual (steps S15 and S17 shown in FIG. 7).

In this modified example, it is possible to specify which of the linear encoder 13 and the encoder 20 has broken down. For this reason, the surgical support device 1 can be reliably retreated using the other of the linear encoder 13 and the encoder 20 which operates as usual, like the first embodiment.

Second Modified Example

Figure 8:
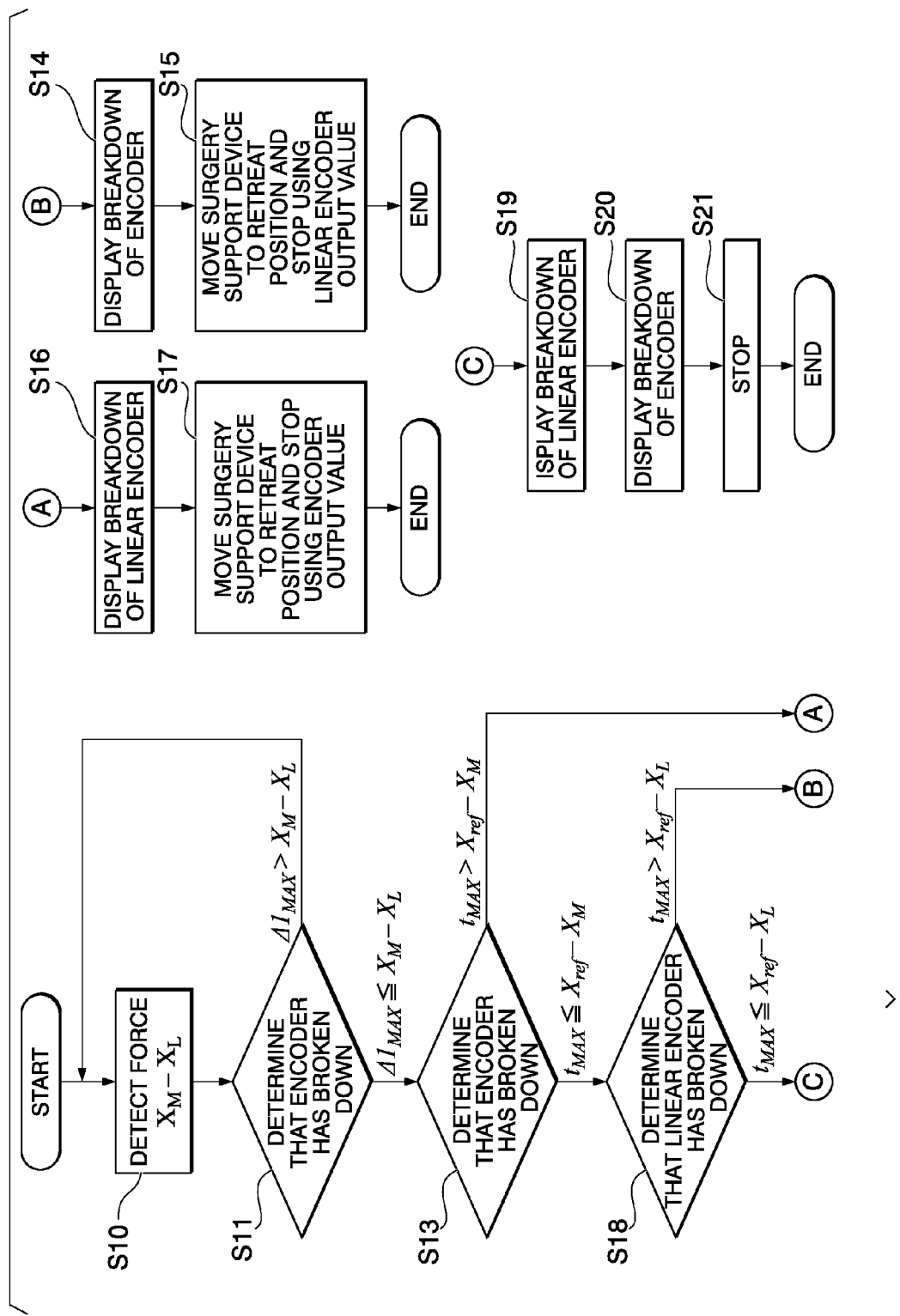
FIG. 8 is a flowchart showing the operation of the surgical support device of a second modified example of the second embodiment of the present invention.

In the first modified example described above, only the breakdown determination of the encoder 20 is performed in the state in which it is determined that at least one of the linear encoder 13 and the encoder 20 has broken down. On the other hand, in this modified example, both the breakdown determination of the encoder 20 and the breakdown determination of the linear encoder 13 may be performed in the state in which it is determined that at least one of the linear encoder 13 and the encoder 20 has broken down (refer to FIG. 8). In this modified example, the breakdown determination of the linear encoder 13 may be performed by the same method as the breakdown determination of the encoder 20 (step S13 shown in FIG. 8). That is, when the case where the difference value obtained by subtracting the output $X_L$, of the linear encoder 13 from the instruction value $X_{ref}$ is the threshold value $t_{MAX}$ or more, the breakdown detection portion 114 determines that the linear encoder 13 has broken down, and then the process proceeds to step S19 (step S18 shown in FIG. 8).

After that, the surgical support device 1 is reliably retreated using the output value from the any one of the linear encoder 13 and the encoder 20 which operates as usual like the first modified example. When it is determined that both the linear encoder 13 and the encoder 20 have broken down by the breakdown detection portion 114, the breakdown detection portion 114 displays information indicating the fact that both the linear encoder 13 and the encoder 20 has broken down, on the master display unit 102 (steps S19 and S20 shown in FIG.

8). After that, the breakdown detection portion 114 may stop all the operation of the slave manipulator 104 (step S21 shown in FIG. 8).

Third Embodiment

Figure 9:
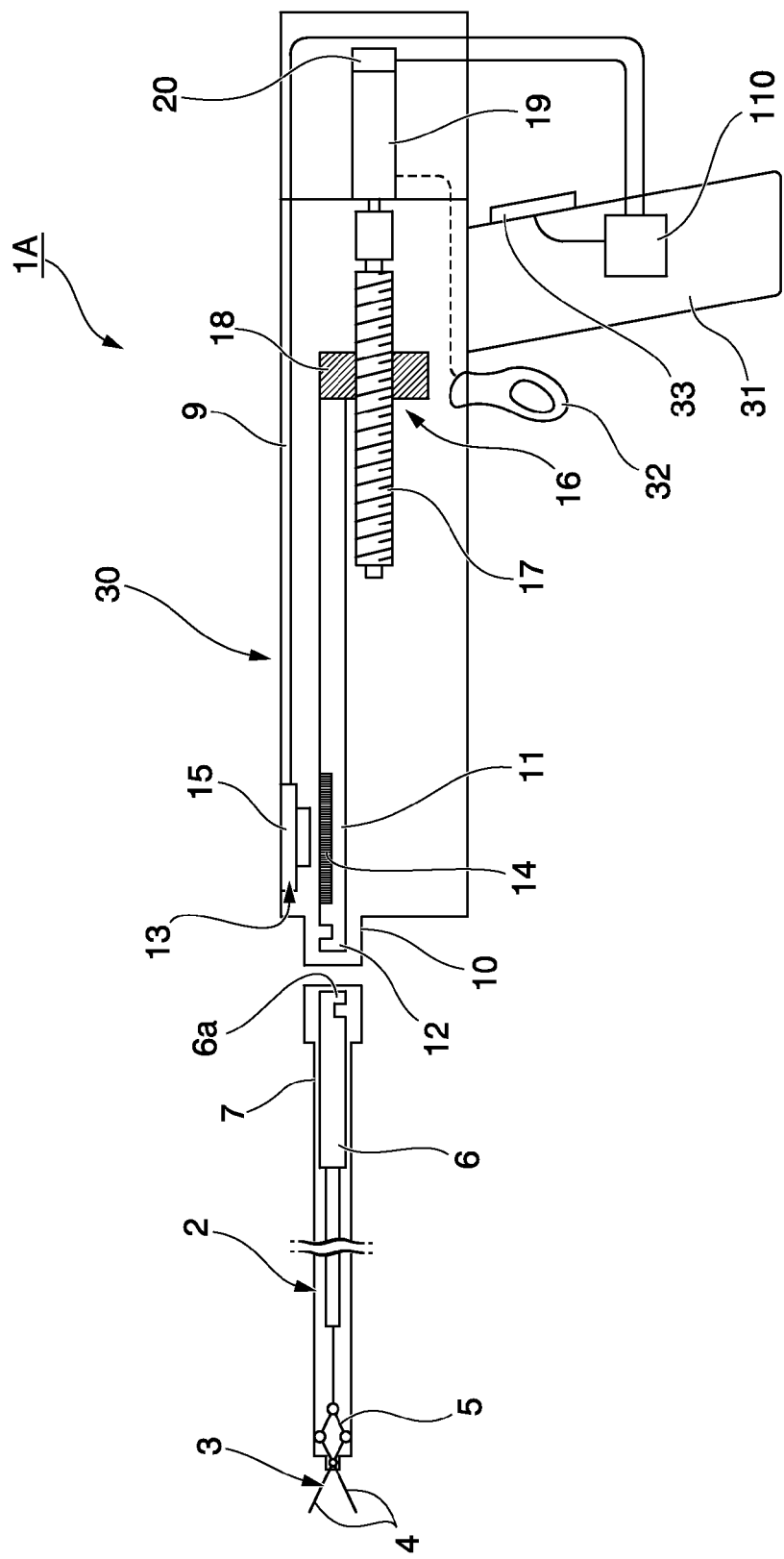
FIG. 9 is a schematic diagram showing a surgical support device of a third embodiment of the present invention.

Next, a surgical support device according to the third embodiment of the present invention will be described. FIG. 9 is a schematic diagram showing the surgical support device according to this embodiment.

The surgical support device 1A of this embodiment is not a part of the surgical support system 100, but is a device held and used by an operator's hand.

As shown in FIG. 9, the surgical support device 1A includes a surgical instrument 2 and a manipulation section 30 installed instead of the slave arm 8.

The manipulation section 30 is different in shape from the slave arm 8 described in the first embodiment, and includes a grip 31 held by the operator, and the overload breakdown detection portion 110 described above.

The grip 31 is provided with a lever switch 32 for outputting the instruction value to the motor 19. As the lever switch 32 is operated, it is possible to instruct a rotational direction, rotational speed, and a rotational amount of the motor 19.

Also, the manipulation section 30 is provided with a status monitor 33 which is electrically connected to the overload breakdown detection portion 110. The overload breakdown detection portion 110 is configured to display on the status monitor 33 the state in which the excessive load is applied, and the state in which the linear encoder 13 or the encoder 20 has broken down.

The surgical support device 1A of this embodiment also has the same effect as those of the surgical support device 1 described in the first embodiment and the second embodiment described above. In addition, since the surgical support device 1A of this embodiment does not necessarily include a force sensor for detecting the force, the surgical support device 1A can be made light in weight. Since the surgical support device 1A held and manipulated by the operator's hand can be made light in weight, it is possible to lighten the operator's burden.

Fourth Embodiment

Next, a surgical support device according to the fourth embodiment of the present invention will be described. The shape of the surgical support device according to this embodiment is substantially the same as that of the surgical support device 1 according to the first embodiment (see FIG. 2).

In the surgical support device 1, the driving rod 11 is linearly moved to open or close the respective grasping pieces of the grasping arm 4. When the moving amount of the driving rod 11 to the proximal end side of the surgical support device 1 exceeds a given defined value, the respective grasping pieces of the grasping arm 4 are in the closed state. Since the respective grasping pieces are not moved in the further closing direction in the state in which the respective grasping pieces are in the closed state, the driving rod 11 is stretched by the force of pulling the driving rod 11. For example, when the stretch of the driving rod 11 is not detected even though it exceeds the defined value, it may be determined that there is a problem, such as breakdown of the driving link 5 or the driven portion 6, in that power is not properly transmitted in the surgical instrument 2 which is disposed at the distal end side rather than the linear encoder 13.

Accordingly, based on the amount of expansion or contraction of the driving rod 11 in correspondence with the moving amount of the driving rod 11 which is detected by use of the linear encoder 13 and the encoder 20, as the amount of stretch of the driving rod 11 which is structurally generated when it operates as usual is set as the threshold value in advance, it is possible to easily detect the problem of the surgical instrument 2 by comparing the moving amount of the driving rod 11 with the threshold value.

In this embodiment, when the difference value in length between the moving amount detected by the linear encoder 13 and the moving amount detected by the encoder 20 is the threshold value or less, it is determined that there is a problem in the surgical instrument 2. As the result, it can be determined not only the breakdown of the slave arm 8 side such as the linear encoder 13 or the encoder 20, but also breakdown of the surgical instrument 2 side.

Although the embodiments of the present invention have been described detail with reference to the accompanying drawings, the concrete configuration is not limited to those of the embodiments, and can include design variations within a scope which does not deviate from the spirit of the present invention.

For example, in the embodiments described above, the driving rod 11 is provided with the linear encoder 13 as the first position detection unit, and the motor 19 is provided with the encoder 20 as the second position detection unit. However, the disposed positions of the first position detection unit and the second detection unit are not limited thereto.

Figure 10:
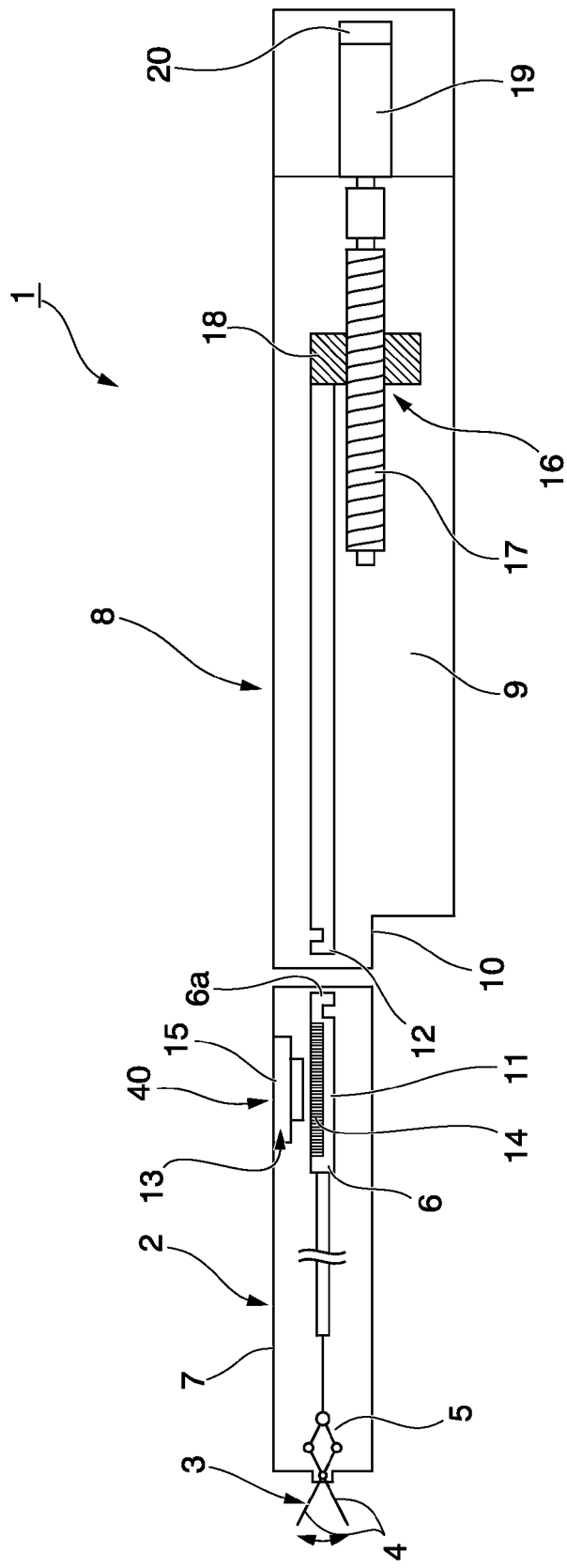
FIG. 10 is a schematic diagram showing a configuration of a surgical support device of another embodiment of the present invention.
Figure 11:
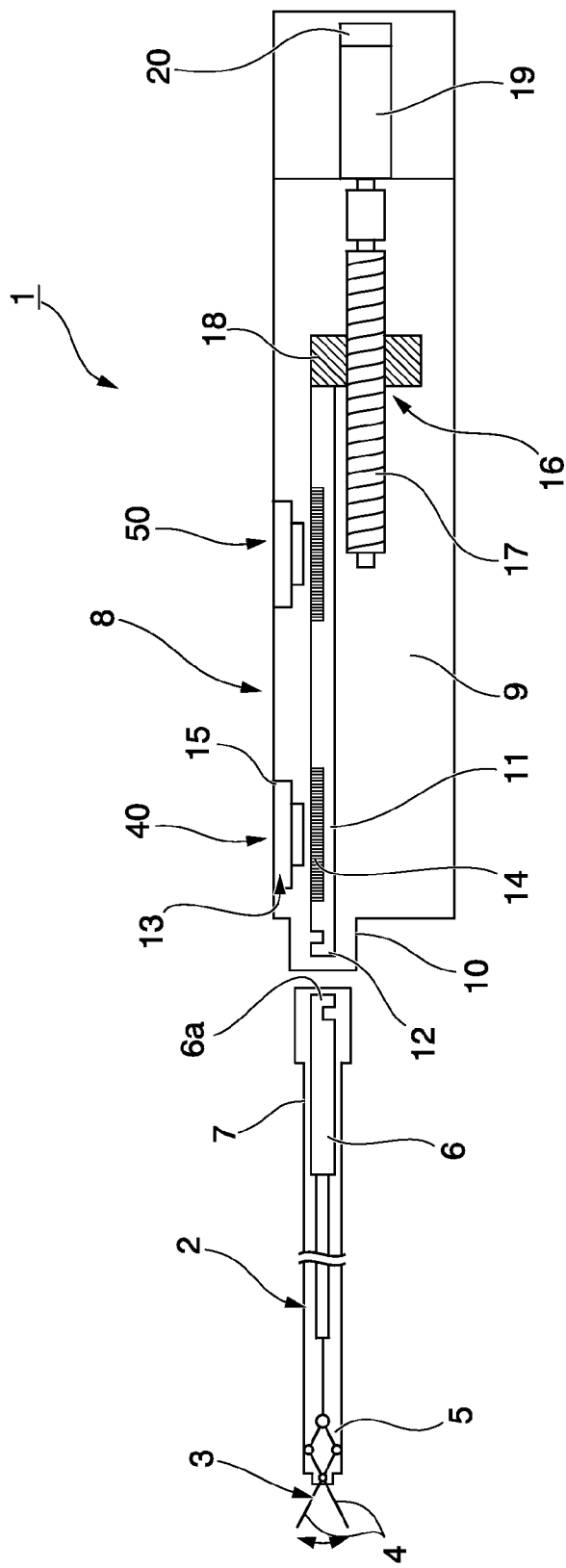
FIG. 11 is a schematic diagram showing a configuration of a surgical support device according to another embodiment of the present invention.
Figure 12:
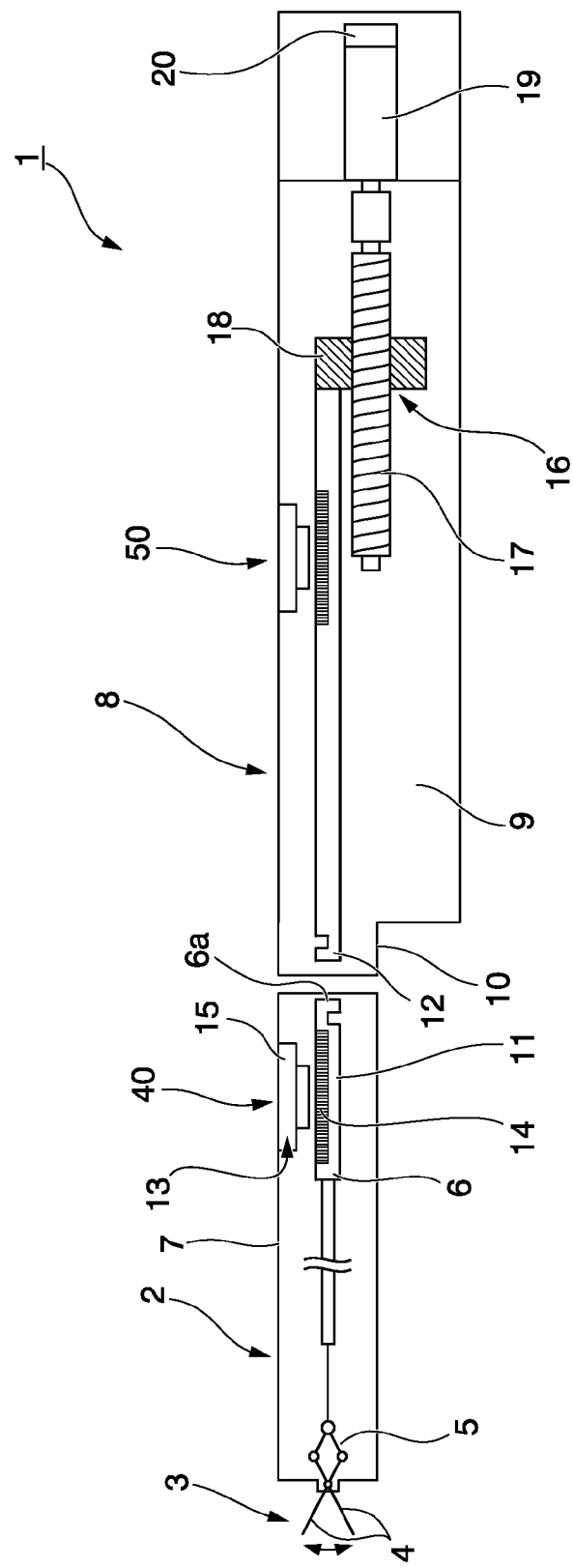
FIG. 12 is a schematic diagram showing a configuration of a surgical support device according to another embodiment of the present invention.
Figure 13:
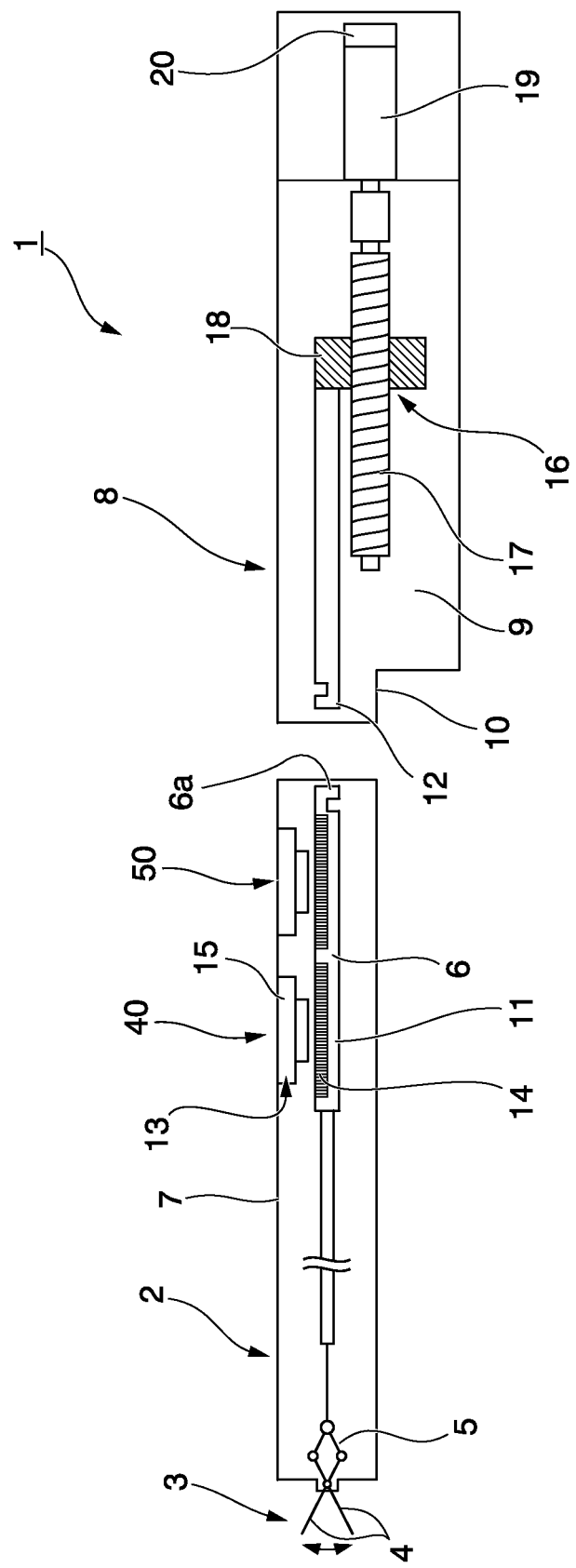
FIG. 13 is a schematic diagram showing a configuration of a surgical support device according to another embodiment of the present invention.

FIGS. 10 to 13 are schematic diagrams showing other configuration examples of the present invention. For example, as shown in FIG. 10, the first position detection unit 40 may be installed on the driven portion 6. Also, as shown in FIG. 11, both the first position detection unit 40 and the second position detection unit 50 may be provided on the driving unit 11. Moreover, as shown in FIG. 12, the first position detection unit 40 may be provided on the driven portion 6, and the second position detection unit 50 may be provided on the driving rod 11. In addition, as shown in FIG. 13, both the first position detection unit 40 and the second position detection unit 50 may be provided on the driven portion 6. In FIGS. 10 to 13, examples in which the first position detection unit 40 and the second position detection unit 50 includes the linear encoder of the same type as the linear encoder 13 described in the first embodiment are shown. In addition, the method for detecting the position in the first position detection unit 40 and the second position detection unit 50 is not specifically limited.

Moreover, in the above embodiment, although an example in which the driving rod 11 and the driven portion 6 are detachably connected to each other is shown, the driving rod and the driven portion may be formed integrally.

In the first embodiment described above, although an example in which the surgical instrument is under the unloaded condition at the initialization of the surgical support system is shown, there is also a case in which a load is applied to the surgical instrument at the initialization of the surgical support system. For example, when the surgical instrument includes forceps, there is a case in which an operator wants to reliably close the forceps at the initialization. In this case, it is necessary to apply some loads to the forceps such that a pair of forceps pieces constituting the forceps are brought into close contact with each other. When the load is applied to the surgical instrument at the initialization, driving states at the initialization and the unloaded condition are defined for every surgical instrument, and a displacement under the unloaded condition may be actually measured based on the original point at the initialization.

In each embodiment described above, an example in which the force is detected by use of two kinds of encoders is shown, but the kind of the respective encoder is not particularly limited thereto. For example, two linear encoders may be used, or the linear encoder and the rotary encoder may be combined.

The methods for determining the state in which the excessive load is applied or determining the breakdown in each embodiment described above can be applied to other sections of the surgical support system. For example, the present invention can be preferably applied to the determination of the presence or absence of the excessive load of the articulated robot 105, or the breakdown determination.

Also, the constitutional elements shown in each embodiment and each modified example described above can be configured by appropriate combination thereof.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. A surgical support device comprising:
   a driving member configured to be driven to transmit a driving force to a target;
   a first sensor configured to detect a first moving amount of the driving member at a first point on the driving member;
   a second sensor configured to detect a second moving amount of the driving member at a second point on the driving member different from the first point on the driving member; and
   a processor comprising hardware, wherein the processor is configured to implement:
      a difference calculation portion configured to calculate a difference in length between the first moving amount and the second moving amount;
      an operating force computing portion configured to compute a magnitude of the driving force transmitted to the target from the driving member based on the difference in length;
      a breakdown detection portion configured to detect at least one of the first sensor and the second sensor has broken down based on the first moving amount and the second moving amount; and
      a control portion configured to control a movement of the driving member based on the detection that at least one of the first sensor and the second sensor has broken down.

2. The surgical support device according to claim 1, wherein the breakdown detection portion is configured to:
   acquire an instruction value of a moving amount for moving the driving member sent to a driving force generating unit configured to drive the driving member;
   determine a first difference value between the instruction value and the first moving amount;
   determine a second difference value between the instruction value and the second moving amount;
   acquire a threshold value determined based on an amount of expansion/contraction of the driving member in correspondence with the instruction value;
   compare the first difference value with the threshold value;
   compare the second difference value with the threshold value;
   determine that the first sensor has broken down based on a determination that the first difference value is equal to or more than the threshold value; and
   determine that the second sensor has broken down based on a determination that the second difference value is equal to or more than the threshold value.

3. The surgical support device according to claim 1, wherein the breakdown detection portion is configured to:
   determine whether the difference in length between the first moving amount and the second moving amount is equal to or more than a predetermined range; and
   detect that at least one of the first sensor and the second sensor has broken down based on a determination that the difference in length between the first moving amount and the second moving amount is equal to or more than the predetermined range.

4. The surgical support device according to claim 3, wherein the breakdown detection portion is configured to:
   acquire an instruction value of a moving amount for moving the driving member sent to a driving force generating unit configured to drive the driving member;
   acquire a threshold value determined based on an amount of expansion/contraction of the driving member in correspondence with the instruction value; and
   when the breakdown detection portion determines that at least one of the first sensor and the second sensor has broken down:
      determine a first difference value between the instruction value and the first moving amount;
      determine a second difference value between the instruction value and the second moving amount;
      compare the first difference value with the threshold value;
      compare the second difference value with the threshold value;
      determine that the first sensor has broken down based on a determination that the first difference value is equal to or greater than the threshold value; and
      determine that the second sensor has broken down based on a determination that the second difference value is equal to or greater than the threshold value.

5. The surgical support device according to claim 3, wherein the breakdown detection portion is configured to:
   acquires an instruction value of a moving amount for moving the driving member sent to a driving force generating unit configured to drive the driving member;
   acquire a threshold value range having a predetermined upper limit and a predetermined lower limit which are determined based on an amount of expansion/contraction of the driving member in correspondence with the instruction value; and
   when the breakdown detection portion determines that at least one of the first sensor and the second sensor has broken down:
      compare a difference value between the instruction value and the second moving amount, with the threshold value range;
      determine that the second sensor has broken down based on a determination that the difference value between the instruction value and the second moving amount is equal to or more than the upper limit of the threshold value range; and
determine that the first sensor has broken down based on a determination that the difference value between the instruction value and the second moving amount is within the threshold value range.

6. The surgical support device according to claim 1, wherein the control portion is configured to stop the movement of the driving member based on a detection by the breakdown detection portion that:
one of the first sensor and the second sensor has broken down, and
the other of the first sensor and the second sensor has not broken down.

7. The surgical support device according to claim 1, wherein in response to the breakdown detection portion detecting that:
one of the first sensor and the second sensor has broken down; and
the other of the first sensor and the second sensor has not broken down,
the control portion is configured to:
move the driving member to a predetermined position while a position of the driving member is detected by the one of the first sensor and the second sensor which has not broken down; and
stop the driving member after the driving member is moved to the predetermined position.

8. The surgical support device according to claim 1, wherein the operating force computing portion is further configured to determine an excessive load state when the magnitude of the force exceeds an upper limit of a predetermined appropriate load.

9. The surgical support device according to claim 1, further comprising:
a surgical instrument configured to perform a treatment on the target; and
a slave arm configured to be detachably connected to the surgical instrument,
wherein slave arm comprises:
the driving member;
the first sensor; and
the second sensor.

10. The surgical support device according to claim 9, wherein the breakdown detection portion is configured to:
refer to a threshold value determined in advance based on an amount of expansion/contraction of the driving member in correspondence with the first moving amount;
determine whether the difference in length is equal to or less than the threshold value; and
determine that the surgical instrument has broken down based on a determination that the difference in length is equal to or less than the threshold value.

11. The surgical support device according to claim 1, further comprising:
a slave arm comprising:
the driving member;
the first sensor; and
the second sensor,
wherein the slave arm is configured to be attached to or detached from an articulated arm.

12. A method for controlling a slave arm, wherein the slave arm comprises:
a driving member configured to be driven to transmit a driving force to a target;
a first sensor configured to detect a first moving amount of the driving member at a first point on the driving member; and
a second sensor configured to detect a second moving amount of the driving member at a second point on the driving member different from the first point on the driving member, and wherein the method comprises:
calculating a difference in length between the first moving amount and the second moving amount;
computing a magnitude of the driving force transmitted to the target from the driving member based on the difference in length;
detecting at least one of the first sensor and the second sensor has broken down based on the first moving amount and the second moving amount; and
controlling a movement of the driving member based on the detection that at least one of the first sensor and the second sensor has broken down.

13. The method according to claim 12, wherein the detecting that at least one of the first sensor and the second sensor has broken down comprises:
acquiring an instruction value of a moving amount for moving the driving member sent to a driving force generating unit configured to drive the driving member;
determining a first difference value between the instruction value and the first moving amount;
determining a second difference value between the instruction value and the second moving amount;
acquiring a threshold value determined based on an amount of expansion/contraction of the driving member in correspondence with the instruction value;
comparing the first difference value with the threshold value;
comparing the second difference value with the threshold value;
determining that the first sensor has broken down based on a determination that the first difference value is equal to or more than the threshold value; and
determining that the second sensor has broken down based on a determination that the second difference value is equal to or more than the threshold value.

14. The method according to claim 12, wherein the detecting that at least one of the first sensor and the second sensor has broken down comprises:
determining whether the difference in length between the first moving amount and the second moving amount is equal to or more than a predetermined range; and
detecting that at least one of the first sensor and the second sensor has broken down based on a determination that the difference in length between the first moving amount and the second moving amount is equal to or more than the predetermined range.

15. The method according to claim 14, wherein the detecting that at least one of the first sensor and the second sensor has broken down comprises:
acquiring an instruction value of a moving amount for moving the driving member sent to a driving force generating unit configured to drive the driving member;
acquiring a threshold value determined based on an amount of expansion/contraction of the driving member in correspondence with the instruction value; and
when detecting that at least one of the first sensor and the second sensor has broken down:

determining a first difference value between the instruction value and the first moving amount;

determining a second difference value between the instruction value and the second moving amount;

comparing the first difference value with the threshold value;

comparing the second difference value with the threshold value;

determining that the first sensor has broken down based on a determination that the first difference value is equal to or greater than the threshold value; and determining that the second sensor has broken down based on a determination that the second difference value is equal to or greater than the threshold value.

16. The method according to claim 14, wherein the detecting that at least one of the first sensor and the second sensor has broken down comprises:

acquiring an instruction value of a moving amount for moving the driving member sent to a driving force generating unit configured to drive the driving member;

acquiring a threshold value range having a predetermined upper limit and a predetermined lower limit which are determined based on an amount of expansion/contraction of the driving member in correspondence with the instruction value; and when detecting that at least one of the first sensor and the second sensor has broken down:

comparing a difference value between the instruction value and the second moving amount, with the threshold value range;

determining that the second sensor has broken down based on a determination that the difference value between the instruction value and the second moving amount is equal to or more than the upper limit of the threshold value range; and determining that the first sensor has broken down based on a determination that the difference value between the instruction value and the second moving amount is within the threshold value range.

17. The method according to claim 12, wherein the controlling the movement of the driving member comprises stopping the movement of the driving member based on a detection that:

one of the first sensor and the second sensor has broken down, and the other of the first sensor and the second sensor has not broken down.

18. The method according to claim 12, wherein the controlling the movement of the driving member comprises:

moving the driving member to a predetermined position while a position of the driving member is detected by the one of the first sensor and the second sensor which has not broken down; and stopping the driving member after the driving member is moved to the predetermined position, in response to a detection that:

one of the first sensor and the second sensor has broken down; and the other of the first sensor and the second sensor has not broken down.

19. The method according to claim 12, further comprising:

determining an excessive load state when the magnitude of the force exceeds an upper limit of a predetermined appropriate load.

20. The method according to claim 12, wherein the slave arm is configured to be detachably connected to a surgical instrument configured to perform a treatment on the target, and wherein the method further comprises:

referring to a threshold value determined in advance based on an amount of expansion/contraction of the driving member in correspondence with the first moving amount;

determining whether the difference in length is equal to or less than the threshold value; and determining that the surgical instrument has broken down based on a determination that the difference in length is equal to or less than the threshold value.

21. A computer-readable storage device storing instructions that when executed by a computer causes the computer to perform a process of controlling a slave arm, wherein the slave arm comprises:

a driving member configured to be driven to transmit a driving force to a target;

a first sensor configured to detect a first moving amount of the driving member at a first point on the driving member; and a second sensor configured to detect a second moving amount of the driving member at a second point on the driving member different from the first point on the driving member, and wherein the process comprises:

calculating a difference in length between the first moving amount and the second moving amount;

computing a magnitude of the driving force transmitted to the target from the driving member based on the difference in length;

detecting at least one of the first sensor and the second sensor has broken down based on the first moving amount and the second moving amount; and controlling a movement of the driving member based on the detection that at least one of the first sensor and the second sensor has broken down.

22. The computer-readable storage device according to claim 21, wherein the detecting that at least one of the first sensor and the second sensor has broken down comprises:

acquiring an instruction value of a moving amount for moving the driving member sent to a driving force generating unit configured to drive the driving member;

determining a first difference value between the instruction value and the first moving amount;

determining a second difference value between the instruction value and the second moving amount;

acquiring a threshold value determined based on an amount of expansion/contraction of the driving member in correspondence with the instruction value;

comparing the first difference value with the threshold value;

comparing the second difference value with the threshold value;

determining that the first sensor has broken down based on a determination that the first difference value is equal to or more than the threshold value; and determining that the second sensor has broken down based on a determination that the second difference value is equal to or more than the threshold value.

23. The computer-readable storage device according to claim 21, wherein the detecting that at least one of the first sensor and the second sensor has broken down comprises:

determining whether the difference in length between the first moving amount and the second moving amount is equal to or more than a predetermined range; and detecting that at least one of the first sensor and the second sensor has broken down based on a determination that the difference in length between the first moving amount and the second moving amount is equal to or more than the predetermined range.

24. The computer-readable storage device according to claim 23,
wherein the detecting that at least one of the first sensor and the second sensor has broken down comprises:
acquiring an instruction value of a moving amount for moving the driving member sent to a driving force generating unit configured to drive the driving member;
acquiring a threshold value determined based on an amount of expansion/contraction of the driving member in correspondence with the instruction value; and
when detecting that at least one of the first sensor and the second sensor has broken down:
determining a first difference value between the instruction value and the first moving amount;
determining a second difference value between the instruction value and the second moving amount;
comparing the first difference value with the threshold value;
comparing the second difference value with the threshold value;
determining that the first sensor has broken down based on a determination that the first difference value is equal to or greater than the threshold value; and
determining that the second sensor has broken down based on a determination that the second difference value is equal to or greater than the threshold value.

25. The computer-readable storage device according to claim 23,
wherein the detecting that at least one of the first sensor and the second sensor has broken down comprises:
acquiring an instruction value of a moving amount for moving the driving member sent to a driving force generating unit configured to drive the driving member;
acquiring a threshold value range having a predetermined upper limit and a predetermined lower limit which are determined based on an amount of expansion/contraction of the driving member in correspondence with the instruction value; and
when detecting that at least one of the first sensor and the second sensor has broken down:
comparing a difference value between the instruction value and the second moving amount, with the threshold value range;
determining that the second sensor has broken down based on a determination that the difference value between the instruction value and the second moving amount is equal to or more than the upper limit of the threshold value range; and
determining that the first sensor has broken down based on a determination that the difference value between the instruction value and the second moving amount is within the threshold value range.

26. The computer-readable storage device according to claim 21,
wherein the controlling the movement of the driving member comprises stopping the movement of the driving member based on a detection that:
one of the first sensor and the second sensor has broken down, and
the other of the first sensor and the second sensor has not broken down.

27. The computer-readable storage device according to claim 21,
wherein the controlling the movement of the driving member comprises:
moving the driving member to a predetermined position while a position of the driving member is detected by the one of the first sensor and the second sensor which has not broken down; and
stopping the driving member after the driving member is moved to the predetermined position,
in response to a detection that:
one of the first sensor and the second sensor has broken down; and
the other of the first sensor and the second sensor has not broken down.

28. The computer-readable storage device according to claim 21,
wherein the process further comprises:
determining an excessive load state when the magnitude of the force exceeds an upper limit of a predetermined appropriate load.

29. The computer-readable storage device according to claim 21,
wherein the slave arm is configured to be detachably connected to a surgical instrument configured to perform a treatment on the target, and
wherein the process further comprises:
referring to a threshold value determined in advance based on an amount of expansion/contraction of the driving member in correspondence with the first moving amount;
determining whether the difference in length is equal to or less than the threshold value; and
determining that the surgical instrument has broken down based on a determination that the difference in length is equal to or less than the threshold value.

* * * * *